(12) United States Patent
Buechler

(10) Patent No.: US 8,597,885 B2
(45) Date of Patent: Dec. 3, 2013

(54) ACCELERATED PROGRESSION RELAPSE TEST

(75) Inventor: Steven Buechler, Granger, IN (US)

(73) Assignee: University of Notre Dame, Notre Dame, IN (US)

( * ) Notice: Subject to any disclaimer, the term of this patent is extended or adjusted under 35 U.S.C. 154(b) by 227 days.

(21) Appl. No.: 12/695,723

(22) Filed: Jan. 28, 2010

(65) Prior Publication Data

US 2010/0196906 A1 Aug. 5, 2010

Related U.S. Application Data

(60) Provisional application No. 61/206,141, filed on Jan. 28, 2009.

(51) Int. Cl.
*C12Q 1/68* (2006.01)
*C12Q 1/00* (2006.01)

(52) U.S. Cl.
USPC ............................. 435/6.11; 435/4; 435/6.1

(58) Field of Classification Search
USPC ............................................ 435/4, 6.1, 6.11
See application file for complete search history.

(56) References Cited

U.S. PATENT DOCUMENTS

| | | | |
|---|---|---|---|
| 7,056,674 | B2 | 6/2006 | Baker et al. |
| 7,171,311 | B2 | 1/2007 | Dai et al. |
| 2007/0105133 | A1 | 5/2007 | Clarke |
| 2009/0311700 | A1* | 12/2009 | Gehrmann et al. ............... 435/6 |
| 2010/0009861 | A1 | 1/2010 | Wang et al. |

FOREIGN PATENT DOCUMENTS

| | | |
|---|---|---|
| WO | WO 2007/062777 | 6/2007 |
| WO | WO 2008/037700 | 4/2008 |
| WO | WO 2008048193 A2 * | 4/2008 |
| WO | WO 2008/077165 | 7/2008 |
| WO | WO 2008/079269 | 7/2008 |

OTHER PUBLICATIONS

Dai et al. Cancer Res. 2005. 65: 4059-4066.*
MacEwen et al. Cancer Res. 1982. 42: 2255-2259.*
Chan. G&P magazine. 2006. 6(3): 20-26.*
Buechler, S. "Low expression of a few genes indicates good prognosis in estrogen receptor positive breast cancer" BMC Cancer 2009 LNKD-PUBMED: 19619298, v. 9, 2009, p. 243.
International Search Report mailed Jul. 9, 2010, PCT/US2010/022403.

(Continued)

*Primary Examiner* — Dave Nguyen
*Assistant Examiner* — Joseph G Dauner
(74) *Attorney, Agent, or Firm* — Thompson Coburn LLP; Denise L. Mayfield

(57) ABSTRACT

An Accelerated Progression Relapse Test (APRT) is provided for use in the prognosis of a diseased state in a patient. The APRT provides a determination of when a patient in a particular diseased state is likely to benefit from further disease treatment, or does not have a high probability of benefit with additional treatment. In particular applications, the APRT may be used to determine the prognosis of an estrogen receptor positive (ER+) breast cancer patient. Four genetic probes are disclosed for this test, and target MK167, CDC6 and SPAG5 gene products. The ER+ breast cancer patient/patient population is stratified into two groups, with the low gene expression group identifying the patient/patient group that is less likely to benefit from additional treatment measures, and a high gene expression group identifying the patient/patient group as more likely to benefit from additional treatment measures.

5 Claims, 13 Drawing Sheets

(56) References Cited

OTHER PUBLICATIONS

Written Opinion of the International Searching Authority mailed Jul. 9, 2010, PCT/US2010/022403.
Ahlin et al., (2007), "Ki67 and cyclin A as prognostic factors in early breast cancer: What are the optimal cut-off values?" Histopathology, 51:491-498.
Bhattacharjee et al., (2001), "Classification of human lung carcinomas by mRNA expression profiling reveals distinct adenocarcinoma subclasses," Proc. Natl. Acad. Sci. USA, 98:13790-13795.
Buechler, (2009), "Low expression of a few genes indicates good prognosis in estrogen receptor positive breast cancer," BMC Cancer, 9:243.
Buyse et al., (2006), "Validation and Clinical Utility of a 70-gene prognostic signature for women with node-negative breast cancer," J. Natl. Cancer. Inst., 98:1183-1192.
Cardoso et al., (2008), "Clinical application of the 70-gene profile: the MINDACT trial," J Clin. Oncol., 26:729-735.
Colozza et al., (2005), "Proliferative markers as prognostic and predictive tools in early breast cancer: where are we now?" Ann. Oncol., 16:1723-1739.
Desmedt et al., (2007), "Strong time dependence of the 76-gene prognostic signature for node negative breast cancer patients in the TRANSBIG multicenter independent validation series," Clin. Can. Res., 13(11):3207-3214.
Du et al., (2008), "Astrin Regulates Aurora-A localization," Biochem Biophys Res Commun, 370(2):213-219.
Eifel et al., (2001), "National Institutes of Health Consensus Development Conference Statement: Adjuvant Therapy for Breast Cancer, Nov. 1-3, 2000," J. Natl. Cancer Inst., 93:979-989.
Fan et al., (2006), "Concordance among gene-expression-based predictors for breast cancer," N. Engl. J. Med., 355:560-569.
Fisher et al., (2004), "Treatment of lymph-node-negative, oestrogen-receptor-positive breast cancer: long-term findings from National Surgical Adjuvant Breast and Bowel Project randomised clinical trials," Lancet, 364: 858-868.
Goldhirsch et al., (2005), "Meeting highlights: international expert consensus on the primary therapy of early breast cancer 2005," Ann. Oncol., 16:1569-1583.
Habel et al., (2006), "A population-based study of tumor gene expression and risk of breast cancer death among lymph node-negative patients," Breast Cancer Res., 8:R25.
Hanahan et al., (2000), "The hallmarks of cancer," Cell, 100:57-70.
Irizarry et al., (2006), "Comparison of Affymetrix Gene Chip Expression Measures," Bioinformatics, 22(7):789-794.
Ivshina et al., (2006), "Genetic reclassification of histogolical grade delineates new clinical subtypes of breast cancer," Cancer Res., 66(21):10292-10301.
Jorgensen et al., (2007), "Pharmacodiagnostics and targeted therapies—a Rational Approach for Individualizing Medical Anti-cancer Therapy in Breast Cancer," The Oncologist, 12(4):397-405.
Kapp et al., (2006), "Discovery and validation of breast cancer subtypes," BMC Genomics, 7:231.
Karakaidos et al., (2004), "Overexpression of the replication licensing regulators hCdt1 and hCdc6 characterizes a subset of non-small-cell lung carcinomas: synergistic effect with mutant p53 on tumor growth and chromosomal instability—evidence of E2F-1 transcriptional control over hCdt1," Am. J. Pathol. 165:1351-65.
Leisch, (2004), "FlexMix: A general framework for finite mixture models and latent class regression in R," Journal of Statistical Software 11:8.
Liontos et al., (2007), "Deregulated overexpression of hCdt1 and hCdc6 promotes malignant behavior," Cancer Res., 67:10899-10909.
Loi et al., (2007), "Definition of clinically distinct molecular subtypes in estrogen receptor positive breast carcinomas through genomic grade," J. Clin. Oncol., 25(10):1239-1246.
Loi et al., (2008), "Predicting prognosis using molecular profiling in estrogen receptor positive breast cancer treated with tamoxifen," BMC Genomics, 9:239.
Martin et al., (2000), "Linking gene expression patterns to therapeutic groups in breast cancer," Cancer Res., 60:2232-2238.
Paik et al., (2004), "A multigene assay to predict recurrence of tamoxifen-treated, node-negative breast cancer," N. Engl. J. Med., 351:2817-26.
Paik et al., (2006), "Gene expression and benefit of chemotherapy in women with node-negative, estrogen receptor-positive breast cancer," J. Clin. Oncol., 24: 3726-3734.
Piccart-Gebhart et al., (2007), "Adjuvant chemotherapy—yes or no? Prognostic markers in early breast cancer," Ann. Oncol., 18(Suppl 12):xii2-7.
Pollok et al., (2007), "Human Cdc45 is a proliferation-associated antigen," FEBS J, 274:3669-3684.
Ramaswamy et al., (2001), "Multiclass cancer diagnosis using tumor gene expression signatures," Proc. Natl. Acad. Sci. USA, 98:15149-15154.
Rizki et al., (2007), "Polo-like kinase 1 is involved in invasion through extracellular matrix," Cancer Res., 67:11106-11110.
Ross et al., (1994), "Ki67: from antibody to molecule to understanding?" J. Clin. Pathol., 48:M113-M117.
Schmidt et al., (2004), "Proliferation marker pKi-67 occurs in different isoforms with various cellular effects," J Cell Biochem., 91:1280-92.
Schmidt et al., (2008), "The human immune system has a key prognostic impact in node-negative breast cancer," Cancer Res., 68(13):5405-5413.
Scholzen et al., (2000), "The Ki-67 protein: from the known and the unknown," J. Cell. Physiol. 182:311-322.
Simpson et al., (2005), "Molecular evolution of breast cancer" J. Pathol., 205:248-54.
Sorlie et al., (2001), "Gene expression patterns of breast carcinomas distinguish tumor subclasses with clinical implications," Proc. Natl. Acad. Sci. USA, 98:10869-10874.
Sotiriou et al., (2006), "Gene expression profiling in breast cancer: understanding the molecular basis of histologic grade to improve prognosis," J. Natl. Cancer Inst., 98:262-72.
Staub et al., (2009), "An expression module of WIPF1-coexpressed genes identifies patients with favorable prognosis in three tumor types," J. Mol. Med., 87(6):633-644.
Taylor et al., (2009), "Dynamic modularity in protein interaction networks predicts breast cancer outcome," Nature Biotechnology, 27(2):199-204.
Tibshirani et al., (2002), "Diagnosis of multiples cancer types by shrunken centroids of gene expression," Proc. Natl. Acad. Sci. USA, 99(10):6567-72.
Tordai et al., (2008), "Evaluation of biological pathways involved in chemotherapy response in breast cancer," Breast Cancer Res. 10:R37.
Van de Vijver et al., (2002), "A gene-expression signature as a predictor of survival in breast cancer," N. Engl. J. Med., 347:1999-2009.
Viale et al., (2008), "Predictive value of tumor Ki-67 expression in two randomized trials of adjuvant chemoendocrine therapy for node-negative breast cancer," J. Natl. Cancer Inst., 100:207-12.
West et al., (2001), "Predicting the clinical status of human breast cancer by using gene expression profiles," Proc. Natl. Acad. Sci. USA, 98:11462-11467.
Wu et al., (2004), "A Model-Based Background Adjustment for Oligonucleotide Expression Arrays," Journal of the American Statistical Association, 99:909-917.
Yan et al., (2001), "Dissecting complex epigenetic alterations in breast cancer using CpG island microarrays," Cancer Res., 61(23):8275-80.
Yeang et al., (2001), "Molecular classification of multiple tumor types," Bioinformatics, 17(Suppl 1):5316-322.
NCBI Gene Expression Omnibus Microarray dataset GSE4922.
NCBI Gene Expression Omnibus Microarray dataset GSE6532.
NCBI Gene Expression Omnibus Microarray dataset GSE7390.
NCBI Gene Expression Omnibus Microarray dataset GSE9195.
NCBI Gene Expression Omnibus Microarray dataset GSE11121.
NCBI Gene Expression Omnibus Microarray dataset GSE12945.

(56) References Cited

OTHER PUBLICATIONS

NCBI Gene Expression Omnibus Microarray dataset GSE17536.
NCBI Gene Expression Omnibus Microarray dataset GSE17537.
National Cancer Institute caARRAY database, dataset public identifier: jacob-00182.
Aubele et al., (2000), "Accumulation of chromosomal imbalances from intraductal proliferative lesions to adjacent in situ and invasive ductal breast cancer," *Diagn. Mol. Pathol.*, 9:14-19.
Golub et al., (1999), "Molecular classification of cancer : class discvery and class prediction by gene expression monitoring," Science, 286:531-537.
Gong et al., (2007), "Determination of the Oestrogen Receptor Status and ERBB2 status of breast carcinoma: a gene expression profiling study," Lancet Oncol., 8:203-211.
Perou et al., (2000), "Molecular portraits of human breast tumors," Nature, 406:747-752.
Shedden et al., (2008), "Gene expression-based survival prediction in lung adenocarcinoma: a multi-site, blinded validation study," Nature Medicine, 14:822-827.
Smith et al., (2010), "Experimentally Derived Metastasis Gene Expression Predicts Recurrence and Death in Patients With Colon Cancer," Gastroenterology, 138(3):958-968, (Nov. 13, 2009, Epublication).
Timofeeva et al., (2009), "Enhanced expression of SOS1 is detected in prostate cancer epithelial cells from African-American men," Int. J. Oncol., 35:751-60.
Yang et al., (2006), "Silencing of astrin induces the p53-dependent apoptosis by suppression of HPV18 E6 expression and sensitizes cells to paclitaxel treatment in HeLa cells," Biochem. Biophys. Res. Commun., 343:428-34.
Zujewski et al., (2008), "Trial assessing individualized options for treatment for breast cancer: the TAILORx trail," Future Oncology, 4:603-610.

* cited by examiner

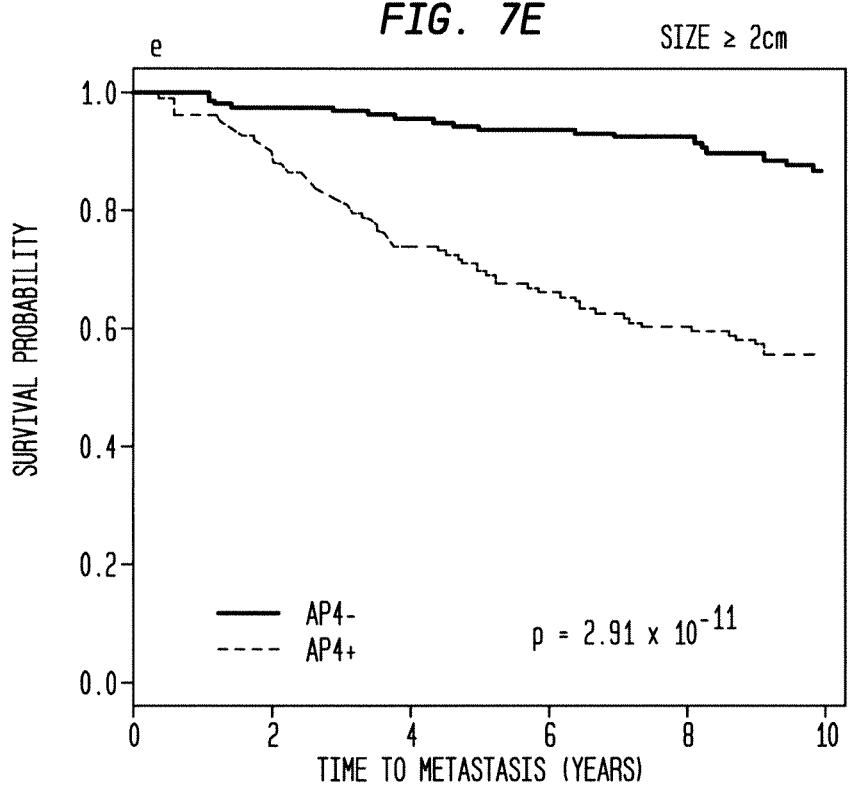
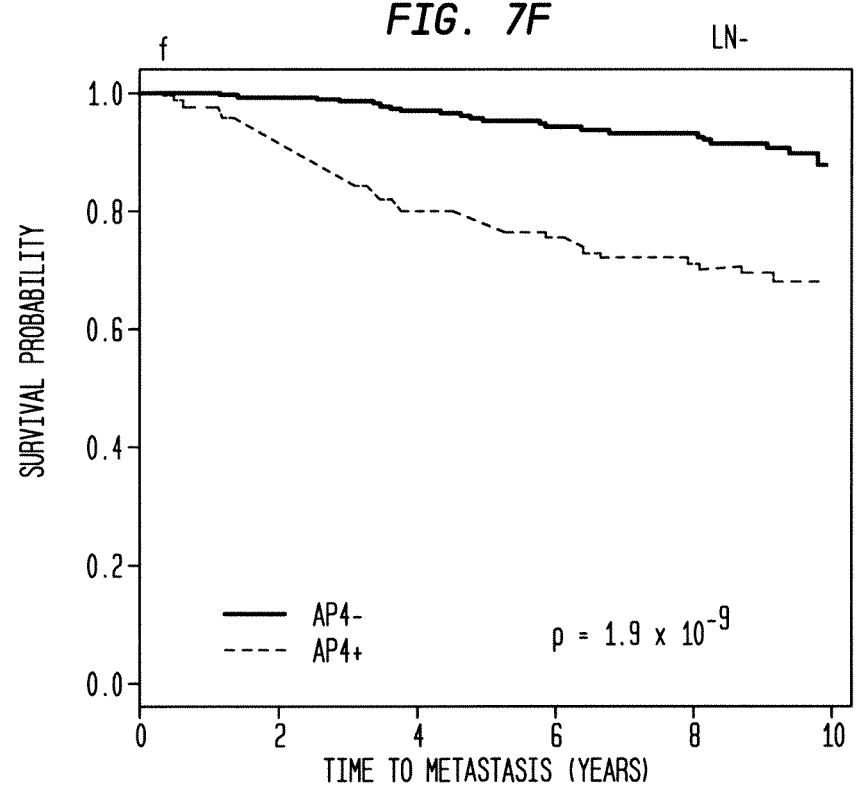

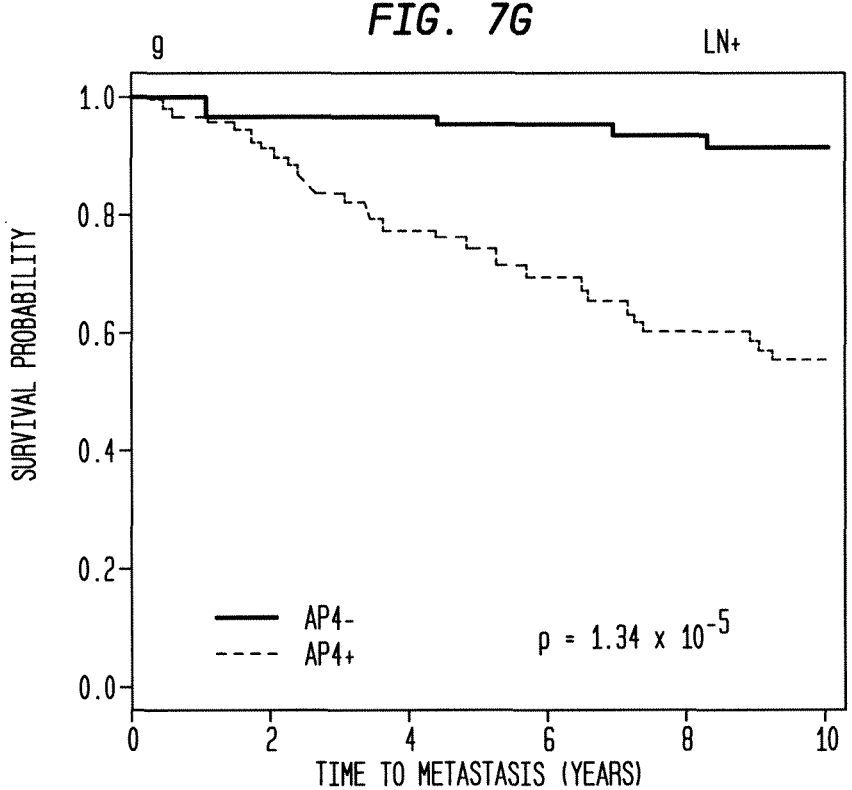
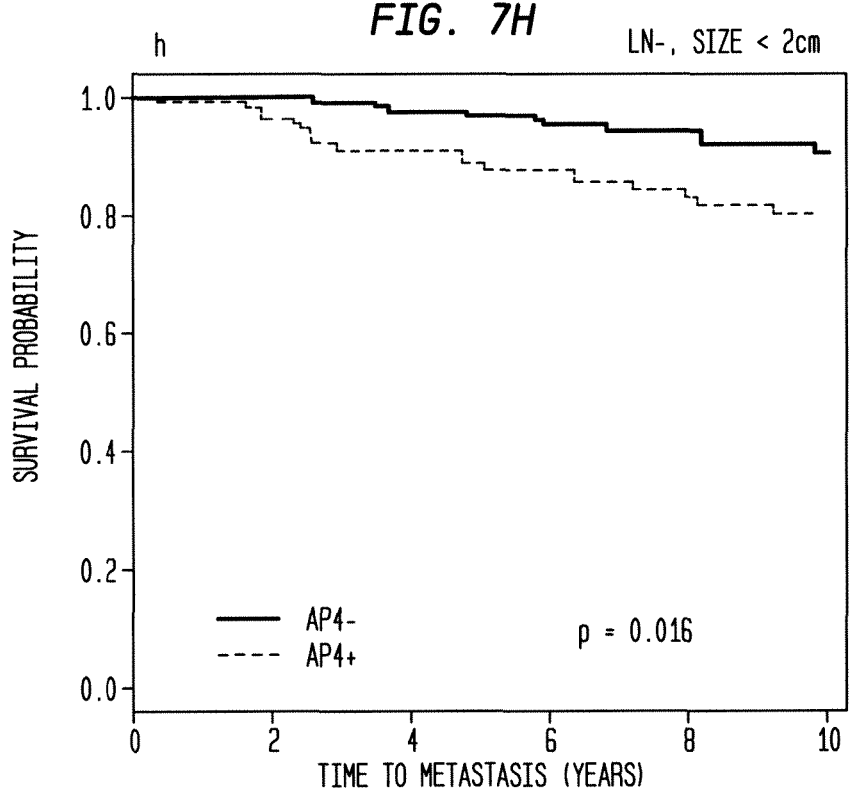

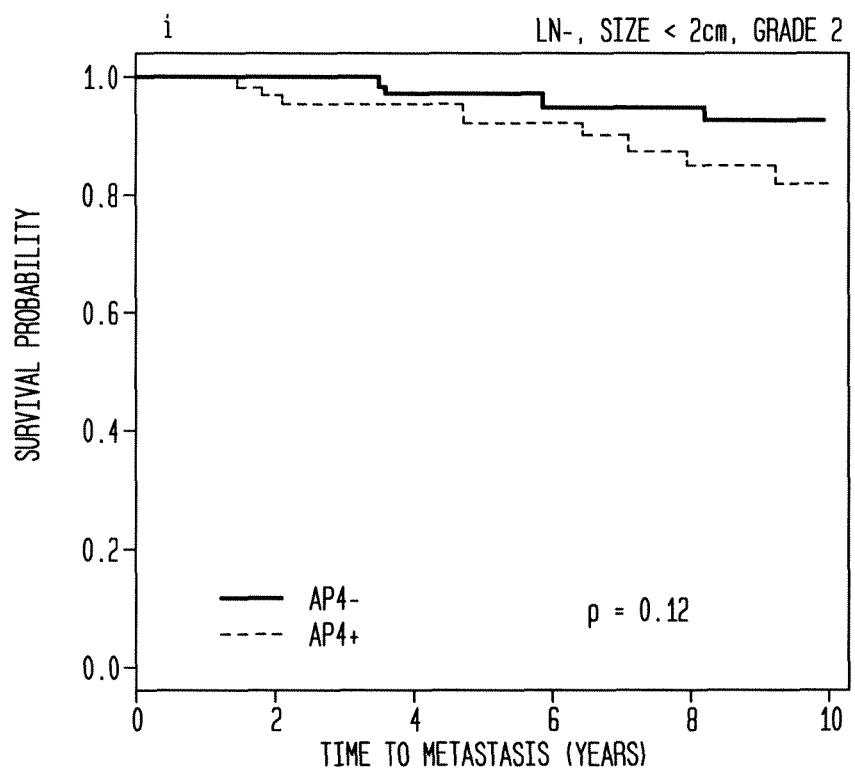

ACCELERATED PROGRESSION RELAPSE TEST

CROSS-REFERENCE TO RELATED APPLICATIONS

This application claims priority to the filing date of provisional U.S. Patent Application No. 61/206,141 entitled "Novel Test for Cancer Recurrence Using the Expression Status of Few Genes," filed Jan. 28, 2009, the entire disclosure and contents of which is incorporated by reference herein.

FIELD OF THE INVENTION

The present invention relates to the field of disease prognostic methods, particularly cancer (breast, colon, lung), and screening tools for determining disease prognosis in a patient.

BACKGROUND

Many breast cancer patients remain free of distant metastasis even without adjuvant chemotherapy. While standard clinical traits fail to identify these good prognosis patients with adequate precision, analyses of gene expression patterns in primary tumors have resulted in more successful diagnostic tests. These tests use continuous measurements of the mRNA concentrations of numerous genes to determine a risk of metastasis in lymph node negative breast cancer patients with other clinical traits. The decision to use adjuvant chemotherapy to treat early-stage breast cancer must balance the reduced risk of recurrence with chemotherapy's toxic effects. The National Surgical Adjuvant Breast and Bowel Project trials B-14 and B-20 suggest that 85% of node-negative, ER+ patients who are treated with tamoxifen alone will be disease free for 10 years (Fisher 2004). Treatment guidelines such as those from the St. Gallen consensus group (Goldhirsch 2005, Eifel 2001) identify a small percentage of patients who can safely forego chemotherapy; however under these guidelines, a significant number of patients undergo chemotherapy unnecessarily.

Methods of stratifying breast cancer patients according to relapse risk have been developed using multi-gene measures of mRNA concentrations. Two tests are the 21-gene screening panel, Oncotype DX® (Genomic Health, Redwood City, Calif.) (Paik 2004, Paik 2006), and the 70-gene array-based test Mammaprint® (Agendia, Amsterdam) (de Vijver 2002, Buyse 2006). These tests apply to node-negative tumors with various other clinical traits. The prospective clinical trial TAI-LORx (Zujewski 2008, Piccart-Gebhart 2007) is testing the ability of Oncotype DX® to identify patients who can safely forego chemotherapy. The MINDACT trial in Europe is a similar test of Mammaprint (Piccart-Gebhart 2007, Cardoso 2008). Both of these tests utilize continuous measurements of mRNA concentrations of numerous genes.

In the past few years, several groups have published studies concerning the classification of various cancer types by microarray gene expression analysis (see, e.g., Golub 1999, Bhattacharjae 2001, Chen-Hsiang 2001, Ramaswamy 2001). Certain classifications of human breast cancers based on gene expression patterns have also been reported (Martin 2000, West 2001, Sorlie 2001, and Yan 2001). However, these studies mostly focus on improving and refining the already established classification of various types of cancer, including breast cancer, and generally do not provide new insights into the relationships of the differentially expressed genes, and do not link the findings to treatment strategies in order to improve the clinical outcome of cancer therapy.

Although modern molecular biology and biochemistry have revealed hundreds of genes whose activities influence the behavior of tumor cells, state of their differentiation, and their sensitivity or resistance to certain therapeutic drugs, with a few exceptions, the status of these genes has not been exploited for the purpose of routinely making clinical decisions about drug treatments. One notable exception is the use of estrogen receptor (ER) protein expression in breast carcinomas to select patients for treatment with anti-estrogen drugs, such as tamoxifen. Another exceptional example is the use of ErbB2 (Her2) protein expression in breast carcinomas to select patients with the Her2 antagonist drug Herceptin™ (Genentech, Inc., South San Francisco, Calif.).

Despite recent advances, the challenge of cancer treatment remains to target specific treatment regimens to pathogenically distinct tumor types, and ultimately personalize tumor treatment in order to maximize outcome. Hence, a need exists for tests that simultaneously provide predictive information about patient responses to the variety of treatment options. This is particularly true for breast cancer, the biology of which is poorly understood. It is clear that the classification of breast cancer into a few subgroups, such as ErbB2$^+$ subgroup, and subgroups characterized by low to absent gene expression of the estrogen receptor (ER) and a few additional transcriptional factors (Perou 2000) does not reflect the cellular and molecular heterogeneity of breast cancer, and does not allow the design of treatment strategies maximizing patient response.

In particular, once a patient is diagnosed with cancer, such as breast or ovarian cancer, there is a strong need for methods that allow the physician to predict the expected course of disease, including the likelihood of cancer recurrence, long-term survival of the patient, and the like, and select the most appropriate treatment option accordingly. To date, no set of satisfactory predictors for prognosis based on the clinical information alone has been identified.

SUMMARY OF THE INVENTION

In a general and overall sense, the present invention provides methods for assessing the relative prognostic value of a cancer treatment for a patient having been diagnosed with a disease, such as cancer. In some embodiments, the method is described as an accelerated progression (AP) relapse test. In some embodiments, the cancer is an estrogen receptor positive (ER+) breast cancer, colon cancer or lung cancer, among others.

In its broadest sense, the present invention provides a method for assessing the relative prognostic value of a cancer treatment for a patient having been diagnosed with cancer based on the level of expression in that patient of certain genes correlated with relapse or recurrence of cancer. According to the invention, those genes most strongly correlated with relapse have a bimodal expression in cancer patients such that those patients expressing a high level of a gene of interest are at high risk for relapse or in need of chemotherapy or other treatment to improve their chances of survival whereas those expressing a low level are not at risk for relapse or in need of treatment such as chemotherapy or the like to improve their chances of survival. In some forms of cancer, and for some genes, low expression levels are associated with poor prognosis and high expression levels with good prognosis. For example, the deletion of a gene or low expression of a gene may cause tumorigenesis in some cancers. These genes that have a bimodal expression in cancer patients and are referred to herein as multi-state genes which are further defined herein. According to the invention, so long as a gene is a multi-state gene, it is useful according to the method of the invention for determining the prognosis of a cancer patient as either being a good prognosis or a bad prognosis.

In one embodiment, a good prognosis may be further defined as having a relatively low expression values for all of the multi-state genes of interest. A poor prognosis may be further defined as having a relatively high expression value for at least one of the selected multi-state genes of interest. A good prognosis further means that a patient is unlikely to benefit from cancer treatment such as chemotherapy or radiation, for example. A poor prognosis further means that a patient is likely to benefit from further cancer treatment such as chemotherapy or radiation, for example. This may be the case where high expression levels are positively correlated with mortality.

In another embodiment, a good prognosis may be further defined as having a relatively high expression value for all of the multi-state genes of interest. A poor prognosis may be further defined as having a relatively low expression value for at least one of the selected multi-state genes of interest. A good prognosis further means that a patient is unlikely to benefit from cancer treatment such as chemotherapy or radiation, for example. A poor prognosis further means that a patient is likely to benefit from further cancer treatment such as chemotherapy or radiation, for example. This may be the case when high expression levels are positively correlated with survival.

According to the invention, one or more multi-state genes from a panel of genes of interest may be selected and the expression levels assayed in a patient in order to determine the patient's prognosis. For example, the expression level of one, two, three, four, five, six, seven, eight, nine, ten, eleven, twelve, thirteen, fourteen, fifteen, sixteen, seventeen, eighteen, nineteen, twenty, thirty, forty, or fifty or more multi-state genes may be ascertained according to embodiments of the invention. The prognosis is based on comparing the patient's expression level to that of the distribution of expression levels of a group of patients having the same cancer. The bimodal distribution when statistically analyzed will have a threshold whereby those patients having expression levels above the threshold have a + status and thereby a poor prognosis and those patients having expression levels below the threshold have a − status and a good prognosis.

In one particular embodiment of the invention, the accelerated progression relapse test is directed to determining the prognosis for ER+ breast cancer patients. According to the methods of the invention, ER+ breast cancer patients are divided into two groups based on the expression values of three genes of interest. For example, in one embodiment, the three genes of interest are MKI67, SPAG5, and CDC6. According to one embodiment of the invention, a gene's expression level is assessed using microarray technology where probes to the genes of interest are present on a microarray. In one embodiment, four microarray probes are utilized to determine the expression level of each of the three genes of interest. For example, in one embodiment, the four probes are 212020_s_at (MKI67.2), 212022_s_at (MKI67), 203967_at. (CDC6) and 203145_at (SPAG5). (These designations are Affymetrix® probe ID numbers). In another embodiment, the four probes are or are derived from mRNA sequences identified by accession number AU152107 (MKI67), BF001806 (MKI67), U77949 (CDC6), and NM_006461 (SPAG5). According to this embodiment, the two groups are AP4+ and AP4−. AP4+ patients have relatively high expression levels of at least one, two, three or four of the genes of interest and have a poor/bad prognosis, whereas AP4− patients have relatively low expression levels of all four genes of interest and have a good prognosis.

As described herein, the +/− status of a patient's gene expression is determined based on comparing that patient's level of gene expression to the density distribution of gene expression from all ER+ patients in a sample group. In one embodiment, density distribution of expression levels from the sample population is determined based on mixture model fit statistical method which is a statistical method know to those of skill in the art. A key discovery according to one aspect of the invention as described herein is that the expression by cancer patients of multi-state genes, as described herein, presents at least a bimodal distribution when the expression level density distribution is determined using the mixture model fit method. Because of this at least bimodal distribution, it is possible to determine a threshold whereby on one side of the threshold, the level of gene expression is low and the prognosis for the patient is good and on the other side of the threshold, the level of gene expression is high and the prognosis for the patient is poor.

In some embodiments, a method is provided comprising comparing the level of gene expression of a defined panel of genes in a patient of interest to gene expression levels of the same panel of genes in a pooled population of ER+ patients, and determining if the patient of interest demonstrates low or high gene expression levels as compared to the distribution of expression levels from the pooled population of patients.

The present invention also provides a gene panel, the expression of which has prognostic value in ER+ breast cancer patients, specifically with respect to disease-free survival. In some embodiments, the gene panel is a panel of three or more genes including CDC6, MKI67 and SPAG5 gene. In another embodiment, the gene panel is a panel of only three genes: the CDC6, MKI67, and SPAG5 genes. In one embodiment, the gene panel includes CDT1, SPAG5, CDC6, and SNRPA1. In another embodiment, the gene panel includes MKI67, SPAG5, PLK1, SNRPA1, and MKI67. In another embodiment, the gene panel includes isoforms of genes in the gene panel.

In some embodiments of the method, a patient having lower levels of gene expression of the defined panel of genes compared to the distribution of expression from the pooled population of patients will be identified as having relatively lower chances of benefiting from subsequent chemotherapy or other cancer treatments. A patient having the same or higher levels of gene expression of the selected panel of genes as compared to the distribution of expression from the pooled population of patients will be identified as having a potentially greater health benefit from subsequent treatment with chemotherapy or other cancer treatment. In some embodiments, the patient is an estrogen receptor positive (ER+) breast cancer patient and the pooled population of patients is a population of ER+ breast cancer patients.

In some embodiments, the assessment of gene expression levels of a defined panel of genes may be measured using GeneChip® or microarray technology. While any number of standard GeneChip® or microarray platforms known to those of skill in the art may be used, an example of one commercially available microarray is the GeneChip® (Affymetrix®).

In some embodiments, the methods are useful in the prognosis of estrogen receptor positive (ER+) breast cancer patients, wherein those with a high enough long-term survival probability according to the method render chemotherapy of questionable benefit. The method is described as the accelerated progression relapse test.

In some embodiments of the method/test, four microarray probes are employed (AP4). In some of the embodiments, two of the probes may be described as targeting MK167, an antigen identified by monoclonal antibody Ki-67. For example, two probes may be used according to the invention to target genes encoding different isoforms of the expression product. Accordingly, in another embodiment, a third probe targets CDC6, a cell division cycle 6 homolog (*S. cerevisiae*). In another embodiment, a fourth probe targets SPAG5, a sperm associated antigen 5. These probes demonstrate distinctive density distributions of expression levels of these genes in samples from ER+ breast cancer patients. For example, with respect to the CDC6 probe, in one embodiment, the distribution divides into two components consisting of a large normal component having low baseline expression of the CDC6 gene, and a long right tail of high expression values of the CDC6 gene as shown in FIG. 1. These two-component expression patterns are suggestive of distinct cellular states.

In some embodiments, nine microarray probes are employed (AP9) to determine the prognosis of an ER+ breast cancer patient. The nine Affymetrix® probes with gene symbol and accession number are: 209832_s_at (CDT1, AF321125), 212020_s_at (MKI67.2, AU152107), 203967_at (CDC6, U77949), 203145_at (SPAG5, NM_006461), 216977_x_at (SNRPA1, AJ130972), 202240_at (PLK1, NM_005030), 212022_s_at (MKI67, BF001806), 208103_s_at (ANP32E, NM_030920), 204817_at (ESPL1, NM_012291). According to this embodiment, if a patient has a high expression level for one of these nine probes, the patient is given a poor prognosis. If the patient has a low expression level for all of these nine probes, the patient is given a good prognosis. In other embodiments, one, two, three, four, five, six, seven, eight, or nine of these multi-state probes are employed in an accelerated progression relapse test.

According to one embodiment of the present method, the method permits patients having been determined to have an ER+ breast cancer to be classified as belonging to one of two groups, one of these groups being a first group comprising the good prognosis group, and a second group comprising a poor prognosis group. The good prognosis group may be further defined as comprising ER+ patients with relatively low expression values for all of the selected expression probes. The poor prognosis group may be further defined as comprising ER+ patients with relatively high expression values for at least one of the selected expression probes. The good prognosis group may be further defined as a group unlikely to benefit from cancer treatment such as chemotherapy or radiation, for example. The poor prognosis group may be further defined as a group likely to benefit from further cancer treatment such as chemotherapy or radiation, for example.

In a general and overall sense, the present invention also provides a method for assessing relapse in ER+ breast cancer. The probes employed as part of the method useful in assessing relapse in the ER+ breast cancer patients may be described as probes that identify the expression of selected genes in the patient sample that have a high correlation with long-term patient survival, and that have expression patterns that group cells into distinctly different biological states. The distinct expression patterns of these selected genes in the poor prognosis and good prognosis group/sets of patients support the observation that the biological pathways that are active in these patients are different. A familiar example is the separation of breast cancer tumors into ER+ and ER− groups. The difference between the two groups is more than a change along a continuum; they represent different processes. Moreover, there is significant evidence that cancer progresses through a series of discrete steps reflecting genetic alterations (Hanahan 2000, Simpson 2005). Genes with expression patterns that divide patients into two groups, one of which is enriched with poor prognosis patients, may be the most direct markers of disease progression.

In yet other embodiments, the invention concerns a method of preparing a personalized genomics profile for a patient, comprising the steps of (a) subjecting RNA, such as mRNA, extracted from a breast tissue obtained from the patient to gene expression analysis; (b) determining the expression level in the tissue of a gene panel comprising CDC6, MKI67 and SPAG5 gene, wherein the expression level is normalized against a control gene or genes and optionally is compared to the amount found in a breast cancer reference tissue set; and (c) creating a report summarizing the data obtained by said gene expression analysis. The normalized expression levels from the patient sample are compared to those in a reference set of samples to determine the prognostic classification of the patient sample.

In one embodiment, the accelerated progression relapse test provides a method for determining a disease prognosis in a patient. The test includes determining expression levels of one or more genes of interest in the patient, determining expression levels of the one or more genes of interest in a patient population having the same disease as the patient, comparing the expression levels from the patient to the expression levels of the population to determine if an expression level of at least one of the one or more genes of interest in the patient is high; and providing the patient a poor prognosis if at least one gene of interest has a high expression level or providing the patient a good prognosis where all of the genes of interest have a low expression level.

According to one embodiment of the AP relapse test, the expression levels of each gene of interest from the patient population forms a density distribution of at least two or more modes and a statistically significant threshold exists between the two or more modes. Expression levels on one side of a defined threshold are deemed high and expression levels on the other side of a defined threshold are deemed low. According to a further embodiment, the density distribution is determined by mixture model fit statistical analysis.

According to one embodiment of the AP relapse test, the expression levels of each gene of interest from the population of patients forms a density distribution of at least two or more modes and a statistically significant threshold exists between the two or more modes. Expression levels on one side of a defined threshold are deemed positively correlated with mortality and expression levels on the other side of a defined threshold are positively correlated with survival. Depending on the gene of interest, some high expression of some genes may be positively correlated with mortality, whereas for other genes, high expression may be positively correlated with survival. According to a further embodiment, the density distribution is determined by mixture model fit statistical analysis.

According to one embodiment of the invention, a poor prognosis comprises prescribing a treatment method to the patient from the group consisting of radiation and chemotherapy, whereas a good prognosis comprises determining that the patient is not in need of treatment. According to different embodiments of the invention, the cancer may be, for example, breast cancer, colon cancer, or lung cancer.

According to a further embodiment of the invention, the expression level of a gene of interest is determined by microarray analysis with mRNA from the patient's tumor. For example, the expression level of a gene can be determined by one or more probes fixed to a microarray chip. In a further embodiment, any one or more of the steps of the AP test is performed by a computer, such as through use of an appropriate software program.

In yet another embodiment, an accelerated progression relapse test is used to determine an ER+ breast cancer prognosis. The steps of the test including determining expression levels of mRNA for a gene panel comprising the CDC6, MKI67, and SPAG5 gene, or their expression products, in a tissue sample of an ER+ breast cancer patient; comparing the expression levels for the patient to expression levels of the gene panel population of ER+ breast cancer patients; and classifying the patient sample as demonstrating a relatively low expression level or a relatively high expression level of the gene panel based on the comparing step; and forming a prognosis of said patient wherein a patient demonstrating a relatively low expression level of the gene panel is provided a prognosis of a sufficiently high long-term metastasis-free survival probability without chemotherapy, and wherein a patient demonstrating a relatively high expression level of at least one gene of the gene panel is provided a prognosis of an increased probability of benefiting from chemotherapy.

According to the invention, the expression levels from the population of cancer patients for each gene in the gene panel comprises a bimodal density distribution such that a statistically significant threshold exists between the two modes, whereby expression levels on one side of the threshold are deemed high and expression levels on the other side of the threshold are deemed low, wherein the patient sample is classified as demonstrating a relatively low expression level or a relatively high expression level based on the expression level as compared to the threshold.

In one embodiment of the AP test, the gene panel further includes the CDT1, PLK1, CDC45L, and SNRP1 genes.

According to another embodiment of the AP test, the step of determining expression levels of mRNA includes utilizing one or more multi-state probes for the CDC6, MKI67, and SPAG5 gene. According to a further embodiment, the one or more multi-state probes for MKI67 can be Affymetrix® probes 212020_s_at and 212022_s_at; the multi-state probe for CDC6 can be Affymetrix® probe 203967_at; and the multi-state probe for SPAG5 can be Affymetrix® probe 203145_at. Alternatively, the probes may be mRNA or fragments thereof of the CDC6, MKI67, and SPAG5 genes or complementary DNA. For example, a probe may be all or a portion of the mRNA found at GenBank Accession No. AU152107 (MKI67), BF001806 (MKI67), U77949 (CDC6), or NM006461 (SPAG5) or the probe may be complementary to all or a portion of the mRNA sequence provided that the probe is specific for and can hybridize to the patient's sample under moderately stringent hybridizing conditions, or in another embodiment, stringent hybridization conditions.

According to a further embodiment, the AP test further includes the step of determining expression levels of mRNA by utilizing one or more multi-state probes for the genes CDT1, PLK1, CDC45L, and SNRP1. According to one embodiment, the multi-state probe for CDT1 is Affymetrix® probe 209832_s_at, the multi-state probe for PLK1 is Affymetrix® probe 202240_at, the multi-state probe for CDC45L is Affymetrix® probe 204126_s_at, and the multi-state probe for SNRP1 is Affymetrix® probe 216977_x_at.

According to a further embodiment of the AP test, calculating an expression level of a gene includes applying GCRMA normalization to the mRNA concentration levels.

According to one embodiment of the AP test, classifying a patient as having a relatively high expression level or a relatively low expression level of the gene panel requires comparing the expression levels for all of the CDC6, MKI67, SPAG5 genes for the patient to a density distribution of gene panel expression levels from the population of ER+ breast cancer patients, the distribution generated using a mixture model fit statistical method to provide a threshold dividing the expression levels into two components where a low expression is below the threshold and high expression is above the threshold.

According to a further embodiment, when a patient demonstrates a relatively low expression level of the gene panel identifies a patient has a high long-term survival probability without receiving chemotherapy or radiation, whereas a patient demonstrating a relatively high expression level of at least one gene of the gene panel identifies that patient as having need of chemotherapy or radiation. The AP test may also include producing a report indicating a prognosis for the patient based on the expression levels and a comparison to other patients with similar expression levels, and optionally, calculating a recurrence score based on the expression levels. According to an embodiment of the invention, any of the steps of the AP test may be performed by a computer. In one embodiment, the expression level of the gene panel is performed by microarray analysis with multi-state probes specific to the genes of the gene panel.

According to a further embodiment, the invention includes a method of determining an ER+ breast cancer prognosis for a patient based on an accelerated progression relapse test. The method includes the steps of determining protein levels of CDC6, MKI67 and SPAG5 genes in a tissue sample of an ER+ patient; comparing the protein levels to protein levels of the CDC6, MKI67, and SPAG5 genes in tissue samples from a population of ER+ patients; based on the comparing step, determining if the protein level is low or high for all of the CDC6, MKI67 and SPAG5 genes; and determining the prognosis of the patient based on the level of each protein being high or low, wherein the patient has good prognosis if each protein level is low or the patient has a poor prognosis if at least one protein level is high. According to one embodiment, the protein levels are determined using immunohistochemical staining.

According to a further embodiment, according to a method of the invention, determining if the protein level is low or high requires comparing the protein expression levels for all of the CDC6, MKI67, SPAG5 genes for the patient to a density distribution of protein expression levels from the population of ER+ breast cancer patients, the distribution generated using a mixture model fit statistical method to provide a threshold dividing the expression levels into two components where a low expression is below the threshold and high expression is above the threshold.

According to a further embodiment, the invention includes a method of preparing a personalized genomics profile for a patient diagnosed with an ER+ breast cancer. The method includes the steps of (a) subjecting RNA extracted from breast cancer cells of the patient to gene expression analysis to determine the expression levels in the cells of mRNA transcripts of CDC6, MKI67, and SPAG5 genes, (b) comparing the expression level of CDC6, MKI67, and SPAG5, wherein the expression level is normalized against a control gene or genes and optionally is compared to the amount found in a breast cancer reference tissue set; and (c) creating a report summarizing the data obtained by said gene expression analysis wherein the report includes a prediction of the likelihood of long term survival of the patient wherein a relatively lower expression level score of the CDC6, MKI67, and SPAG5 genes indicates a increased likelihood of long-term survival without breast cancer recurrence. In one embodiment, the breast tissue is obtained from a fixed, paraffin-embedded biopsy sample. In a further embodiment, the report includes recommendation for a treatment modality of said patient.

According to another embodiment, the invention includes a method of determining the prognosis of an ER+ breast cancer patient which includes subjecting a tumor tissue sample of said patient to a protein staining technique to determine expression level of proteins encoded by the CDC6, MKI67, and SPAG5 genes; subjecting tumor tissues samples from a population of ER+ breast cancer patients to said protein staining technique to determine density distribution of expression levels of proteins encoded by the CDC6, MKI67, and SPAG5 genes in said population; comparing the expression levels of said patient to the density distribution of said population to determine a prognosis for the said patient. When the patient is provided a prognosis of a sufficiently high long-term metastasis-free survival probability without chemotherapy when the patient demonstrates a relatively low expression level of said genes, and wherein when the patient is provided a prognosis of an increased probability of benefiting from chemotherapy when the patient demonstrates a relatively high expression level of said genes.

According to another embodiment of the invention, the invention includes a method of providing an ER+ breast cancer prognosis to a patient based on an accelerated progression relapse test. The test includes the steps of (a) taking a breast tumor tissue sample from the patient, (b) determining the expression level of each CDC6, MKI67, and SPAG5 in the tissue sample; (c) comparing the expression level of CDC6, MKI67, and SPAG5, to a reference set of expression levels from a cohort of ER+ breast cancer patients to determine whether the expression level of each gene is low or high in comparison to the reference set; and (d) creating a report summarizing the data obtained by the accelerated progression relapse test, wherein the report includes a prediction of the likelihood of long term survival of the patient wherein the patient is given a prognosis of an increased likelihood of long-term survival without breast cancer recurrence if the expression level of the CDC6, MKI67, and SPAG5 genes is low and wherein the patient is given a prognosis of a decreased likelihood of long-term survival with breast cancer recurrence or metastasis and a prescription for chemotherapy if the expression level of at least one of CDC6, MKI67, and SPAG5 is relatively high. According to one embodiment of the invention, the expression levels of the CDC6, MKI67, and SPAG5 genes is determined by utilizing probes specific for mRNA or cDNA encoding the CDC6, MKI67, and SPAG5 genes. For example, the probes may be affixed to a microarray device. In an alternative embodiment, the expression levels are determined by immunohistochemical staining of the patient's tissue sample.

According to another aspect, the invention employs a computer to perform the AP test of the invention. For example, in one embodiment, a computer running a software program analyzes gene expression level data from a patient, compares that data to a distribution of expression levels from a population of patients having the same disease state, and determines whether the patient's expression levels have a +/− AP status for each gene of interest. Based on the AP status for each gene, the computer software is capable of determining the prognosis for the patient as being good or poor. For example, the software is capable of generating a report summarizing the patient's gene expression levels and/or the patient's AP status scores, and/or a prediction of the likelihood of long term survival of the patient and/or the likelihood of recurrence or metastasis of the patient's disease condition, for example, cancer. Further, in one embodiment, the computer program is capable of performing any statistical analysis of the patient's data or a population of patient's data as described herein in order to generate the AP status of the patient. Further, in one embodiment, the computer program is also capable of normalizing the patient's gene expression levels in view of a standard or control prior to comparison of the patient's gene expression levels to those of the patient population. Further, in one embodiment, the computer is capable of ascertaining raw data of a patient's expression values from, for example, immunohistochemical staining or a microarray, or, in another embodiment, the raw data is input into the computer.

For the purpose of describing the present invention, a multi-state gene is formalized in a dataset of mRNA expression values. A data set of mRNA expression values may be generated using, for example, an Affymetrix® GeneChip® microarray. One array may be generated for each patient in the cohort. Consider an array probe p such that increased expression is statistically significant in a univariate Cox proportional hazard model of relapse.

For purposes of the present methods, "p" is designated multi-state in this cohort if the density distribution can be partitioned into two components: a large normal component of expression values below a threshold c, and a long right tail with expression values above c. The component of high expression values, denoted "p+", contains a greater percentage of patients who relapse than the component of low expression values, denoted "p−".

FIG. 1 shows an example of a multi-state probe for CDC6 in one patient cohort. For a probe p such that decreased expression is correlated with relapse, the roles of p+ and p− are reversed, and p− consists of a long left tail. The statistical theory of mixture models is used to decide if a probe is multi-state, and to find an optimal threshold between the low and high components (see Methods). A survival model based on several multi-state probes, $p_1, \ldots, p_n$, distinguishes the samples in the intersection of the good prognosis groups of all $p_i$'s, from the others.

According to one embodiment, the method of the invention is an accelerated progression relapse test. In one embodiment, an accelerated progression relapse test is developed using a multi-state probe methodology. Given a microarray dataset of ER+ breast cancer samples, for example, an Affymetrix®-generated protein microarray set of data, the samples are partitioned into groups AP4+ and AP4−, where AP4− consists of those samples with low expression for each of the 4 multi-state probes 212020_s_at (probe for MKI67), 212022_s_at (probe for MKI67), 203967_at (probe for CDC6), and 203145_at (probe for SPAG5). These probes represent the genes MKI67 (2 probes targeting genes for two isoforms), CDC6 and SPAG5. In the training set used to derive the test, no continuous expression vector is a significant predictor of relapse in the AP4− group. Similarly, no multi-state probe negatively correlated with relapse improves the fit by AP4+/−. FIG. 2 contains a Kaplan-Meier survival plot for the AP4+/− groups in a validation set of 475 samples. In a generalization of the AP4 test beyond this study a new sample would be classified as AP4+ or AP4− using cutoffs defined with a reference set of samples. A Monte Carlo cross validation test calculates the mean misclassification rate to be 0.0335±0.0005 (1 s.e.). This high level of stability of the cutoffs is not surprising given the sharp boundaries between the high and low components in multi-state probes.

The methodology leading to the AP4 test actually identifies several alternative models with comparable hazard ratios in the samples used here. These alternatives use, for example, 4 to 7 probes, chosen from the AP4 probes CDC6, MKI67, SPAG5 and ones representing CDT1 (chromatin licensing and DNA replication factor 1), PLK1 (polo-like kinase 1), CDC45L (CDC45 cell division cycle 45-like (*S. cerevisiae*)), and SNRPA1 (small nuclear ribonucleoprotein polypeptide A'). Most of these genes are directly involved in mitosis, consistent with the central role of cell cycle progression in ER+ breast cancer relapse. Reports of poor prognosis in carcinomas with elevated expression of these genes are widespread.

Typical of models of relapse in ER+ breast cancer, there is a high positive correlation between AP4+/− and tumor grade (Pearson's chi-squared test p-value <$2.2 \times 10^{-16}$, in all samples used here.) In fact, tumor grade is not a significant predictor of metastasis on AP4− or on AP4+; i.e., the ability of tumor grade to predict metastasis is captured by AP4+/−. Lymph node status has the same relationship. A binary variable for tumor size is defined using a cutoff of 2 cm. Tumor size is not a significant predictor of metastasis on AP4−, but is significant on AP4+ (logrank score p-value=$7.56 \times 10^{-6}$). Table 1 reports the impact of clinical variables on metastasis-free survival probabilities on AP4− and AP4+.

TABLE 1

| Clinical Trait | Number | 5 year survival with 95% CI | 10 year survival with 95% CI |
|---|---|---|---|
| AP4− | 339 | 0.95 (0.93-0.98) | 0.89 (0.85-0.93) |
| Grade 1 | 106 | 0.99 (0.97-1.0) | 0.91 (0.83-0.99) |
| Grade 2 | 179 | 0.93 (0.89-0.97) | 0.87 (0.82-0.93) |
| Grade 3 | 20 | 0.90 (0.77-1.0) | 0.90 (0.77-1.0) |
| Grade NA | 34 | | |
| Size <2 cm | 156 | 0.97 (0.94-1.0) | 0.92 (0.87-0.97) |
| Size >2 cm | 180 | 0.94 (0.90-0.98) | 0.87 (0.81-0.93) |
| Size NA | 3 | | |
| LN negative | 268 | 0.95 (0.93-0.98) | 0.88 (0.84-0.93) |
| LN positive | 71 | 0.95 (0.90-1.0) | 0.91 (0.84-0.99) |
| AP4+ | 399 | 0.77 (0.73-0.82) | 0.65 (0.60-0.70) |
| Grade 1 | 45 | 0.90 (0.80-1.0) | 0.70 (0.55-0.88) |
| Grade 2 | 200 | 0.75 (0.69-0.82) | 0.63 (0.56-0.72) |
| Grade 3 | 108 | 0.72 (0.64-0.81) | 0.64 (0.55-0.74) |
| Grade NA | 46 | | |
| Size <2 cm | 144 | 0.88 (0.82-0.93) | 0.80 (0.73-0.88) |
| Size >2 cm | 251 | 0.70 (0.64-0.76) | 0.56 (0.49-0.63) |
| Size NA | 4 | | |
| LN negative | 279 | 0.78 (0.73-0.83) | 0.68 (0.63-0.75) |
| LN positive | 120 | 0.74 (0.66-0.83) | 0.56 (0.46-0.67) |

The interaction between AP4+/− and histopathological traits are detailed by calculating the metastasis-free survival probabilities for each subgroup. It shows no significant change in survival probability for AP4− across all groups. The only significant effect is for tumor size on AP4+.

A prospective trial will be performed to verify that AP4− patients do not significantly benefit from chemotherapy, this hypothesis is supported by the data and studies of chemo-sensitivity; i.e., the likelihood that a tumor will respond positively to chemotherapy. The NSABP B-20 trial (Fisher 2004) reports that ER+ node-negative patients receiving cyclophosphamide, methotrexate, fluorouracil and tamoxifen (CMFT) have a 12-year overall survival probability of 0.87. This probability is comparable to the AP4-10-year metastasis-free survival probability of 0.90 (95% CI 0.85-0.93). However, it is important to know that the AP4− tumors that eventually metastasize are not those that will benefit the most from chemotherapy. The genomic grade index (GGI) (Sotiriou 2006), a test for recurrence in ER+ breast cancer that is highly enriched with cell cycle progression genes, is also correlated with chemo-sensitivity (Tordai 2008). As FIG. 3a shows, only a few AP4− samples have GGI values above the mean of 0. Moreover, TOP2A, a target for anthracyclines, is expressed at a low level throughout AP4− tumors (FIG. 3b).

There is significant synergy between the use of MK167 in the AP4 test and the Ki-67 proliferation index (Scholzen 2000). The Ki-67 proliferation index for a tissue sample is the percentage of cells that respond positively to the MIB-1 antibody using immunohistochemistry (IHC), also called the labeling index for Ki-67. A sample has a low Ki-67 index if the labeling index is below a certain cutoff, and has a high Ki-67 index otherwise. Common choices for the cutoff are 10% or the median value over a cohort (typically 17% to 19%). The present of mixture models to divide multi-state probe expression levels into low and high components informs the cutoff selection for the Ki-67 labeling index. FIG. 4 plots the distribution of labeling indices for Ki-67 in the ER+ samples from Trial IX of the International Breast Cancer Study Group (Viale 2008), and the distribution of MK167 expression levels. This predictable similarity in distributions suggest that Ki-67 labeling indices can be divided into low and high components using the mixture model methods applied to multi-state probes. Doing so identifies a cutoff of 23%, close to the seventh decile, 22%. A Ki-67 cutoff at the seventh decile was shown to yield the highest hazard ratio for metastasis-free survival (Ahlin 2007). Thus, a partition of samples with the multi-state probe methodology may yield the optimal input of MK167 (Ki-67) in a model of metastasis.

Previous research on several of the genes in this study reports that expression patterns of the genes divide tumor tissues into two distinct groups, supporting the presenting disclosed multi-state methodology. Expression of CDC6 in non-small cell lung cancer (NSCLC) cells, as assessed with RT-PCR, partitions cells into two groups, one with baseline expression, and a second group with highly elevated expression (Karakaidos 2004). These two groups were also identified with IHC[24]. Similar patterns were found for CDT1 (Karakaidos 2004). Using IHC, PLK1 was detected at a high level in invasive carcinomas of the breast and undetected in normal breast tissue (Rizki 2007). Elevated expression of CDC6 and CDTI in NSCLC is frequently caused by gene amplification (Liontos 2007) (at 17q21.3 and 16q24.3, respectively), although there are apparently other causes. Other genes used in this study are located at known sites of somatic mutation in breast cancer (Aubele 2000, Simpson 2005), MK167 (10q25-qter), SPAG5 (17q11.2), PLK1 (16p12.1), SNRPA1 (15q26.3), CDC45L (22q11.21). However, the nature of the relationship between +/− status and somatic mutation remains open.

The ability to use IHC to distinguish thresholds between low and high expression levels of genes used in the present invention supports the use of the accelerated progression relapse test with immunohistochemistry (IHC). Such a multi-gene extension of the Ki-67 proliferation index would be a straightforward test for the benefit of administering chemotherapy.

The methodology leading to the AP4 test actually identifies a family of models with comparable hazard ratios in the samples used here. These alternatives use 4 to 7 probes, chosen from those defining AP4 and probes representing CDT1 (chromatin licensing and DNA replication factor 1), PLK1 (polo-like kinase 1), CDC45L (CDC45 cell division cycle 45-like (*S. cerevisiae*)), and SNRPA1 (small nuclear ribonucleoprotein polypeptide A'). Most of these genes are directly involved in mitosis, consistent with the central role of cell cycle progression in ER+ breast cancer relapse. Reports of poor prognosis in carcinomas with elevated expression of these genes are widespread. While MKI67 and CDC6 have been widely studied, the other gene in the AP4 test, SPAG5 is less well-known. Also known as Astrin, SPAG5 codes a protein involved in mitotic spindle assembly. Silencing of SPAG5 induces p53-mediated apoptosis and sensitizes cells to paclitaxel treatment in HeLa cells. In Du 2008 it is shown that SPAG5 interacts with AURKA (STK15). Both MKI67 and AURKA are found in the Oncotype DX® panel.

Using the results in this study, the AP4 test could be implemented with a reference set of microarrays. A patient would be tested by hybridizing mRNA from the tumor to a microarray, applying GCRMA to this microarray and the reference set together, and determining the sample's AP4 status using cutoffs determined with the reference samples. However, full genome microarrays are comparatively expensive and generate a huge amount of information that is not used in determining AP4 status. The development of a clinically useful form of the AP4 test requires (1) selection of a method for measuring the mRNA concentration or protein levels of the associated genes, (2) analysis of the density distribution of these measures and selection of cutoffs using the mixture model method, and (3) determination of the long-term expected survival probability for the AP4− group calculated using the cutoffs from (2). While the most direct method would use RT-PCR or a custom microarray to measure the mRNA levels, it is likely that some test in the accelerated progression family can be implemented with IHC.

Some of the advantages of the AP Relapse Test include providing prognostic information comparable to competing tests at a fraction of the price.

The unique features of this test include, by way of example, the following characteristics among others:
1. As few as three genes are used in determining AP status.
2. Only the +/− status of a gene is required. It is critical that these genes are multi-state. Recognition of this property of expression distributions is novel.
3. The +/− status of the genes may be determined with immunohistochemistry (IHC).
4. The AP relapse test is equally applicable to lymph node positive (LN+) and lymph node negative (LN−) breast cancer patients.
5. The AP relapse test provides greater prognostic power than other commercially available tests.

In 6(b), AP4− denotes a good prognosis group that includes samples/sample population that exhibit a low expression component for each of the 4 multi-state probes of interest, CDC6− denotes a sample/sample population having a low expression component of CDC6 gene product, AP4+ denotes a poor prognosis group which includes samples wherein at least one of the four multi-state probes of interest is high, and the prognosis is poor, and CDC6+ denotes a sample/sample population demonstrating a high expression component of CDC6 gene product. In 6(d), AP4− denotes a good prognosis group of samples that exhibit a low expression component for each of the 4 multi-state probes of interest, SPAG5− denotes a sample/sample population having a low expression component of SPAG5 gene product, AP4+ denotes a poor prognosis group which includes samples wherein at least one of the four multi-state probes of interest is high, and SPAG5+ denotes a sample/sample population having a high expression component of SPAG5 gene product.

FIG. 7: According to one aspect of the invention presents Kaplan-Meier survival plot for AP4 in clinical subtypes. The domain for this analysis is the set of 738 samples for which data exists on distant metastasis, grade, tumor size and node status. Each plot is for AP4 in the subtype indicated above the panel. These clinical variables do not improve on the prognostic power of AP4−. In fact, tumor grade is not a significant predictor of metastasis on AP4– or on AP4+; i.e., the ability of tumor grade to predict metastasis is completely captured by AP4+/–. Lymph node status has the same relationship. Tumor size is not a significant predictor of metastasis on AP4–, but is significant on AP4+ (p-value=$7.56 \times 10^{-6}$.)

Figure 7A:
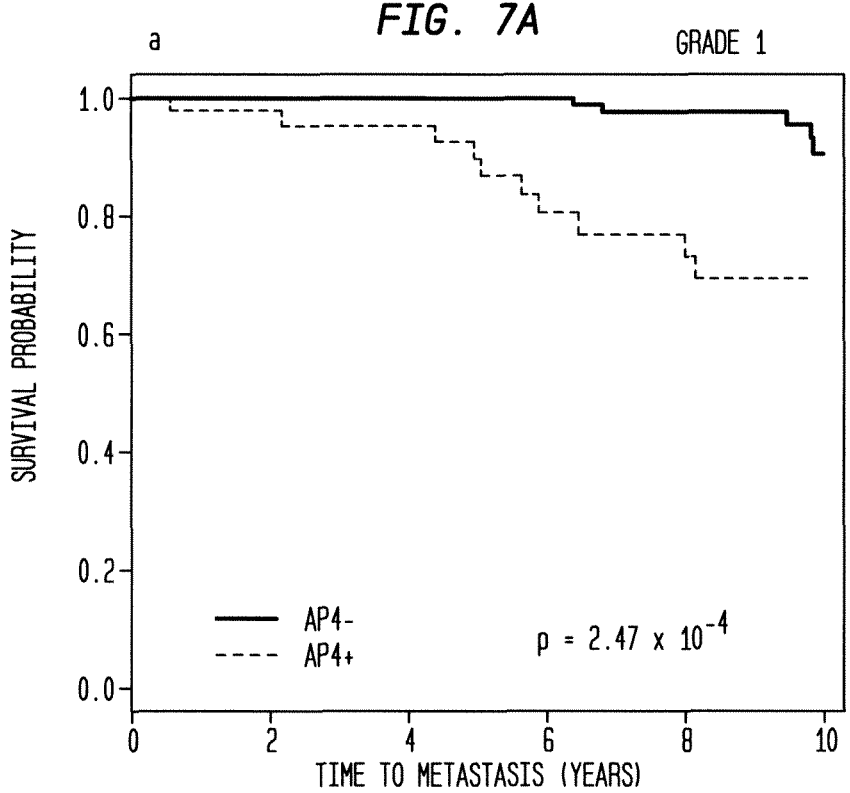
Figure 7B:
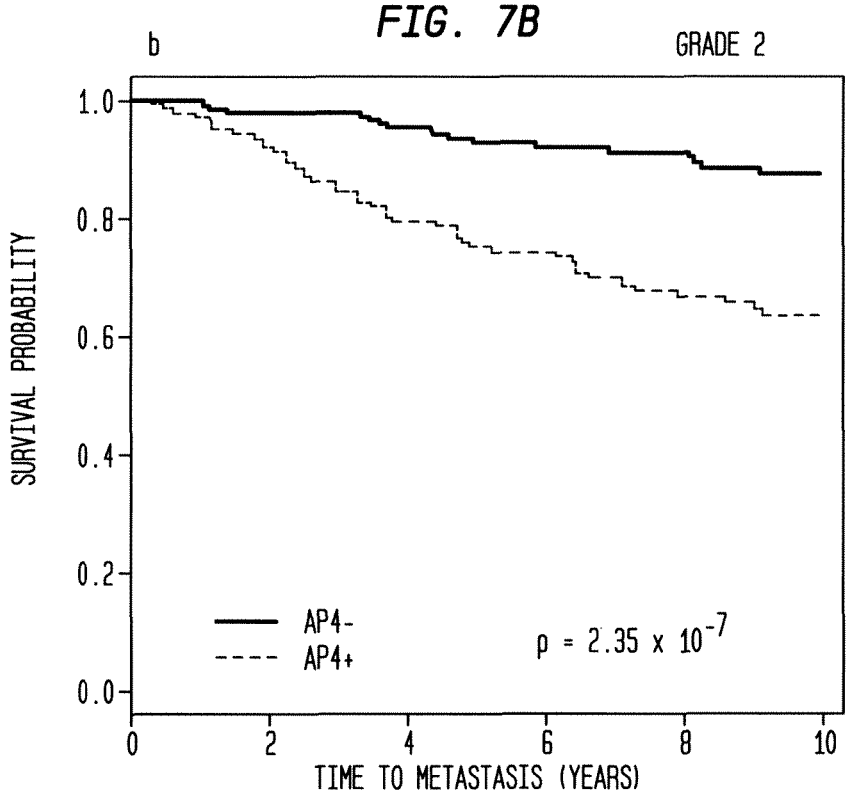
Figure 7C:
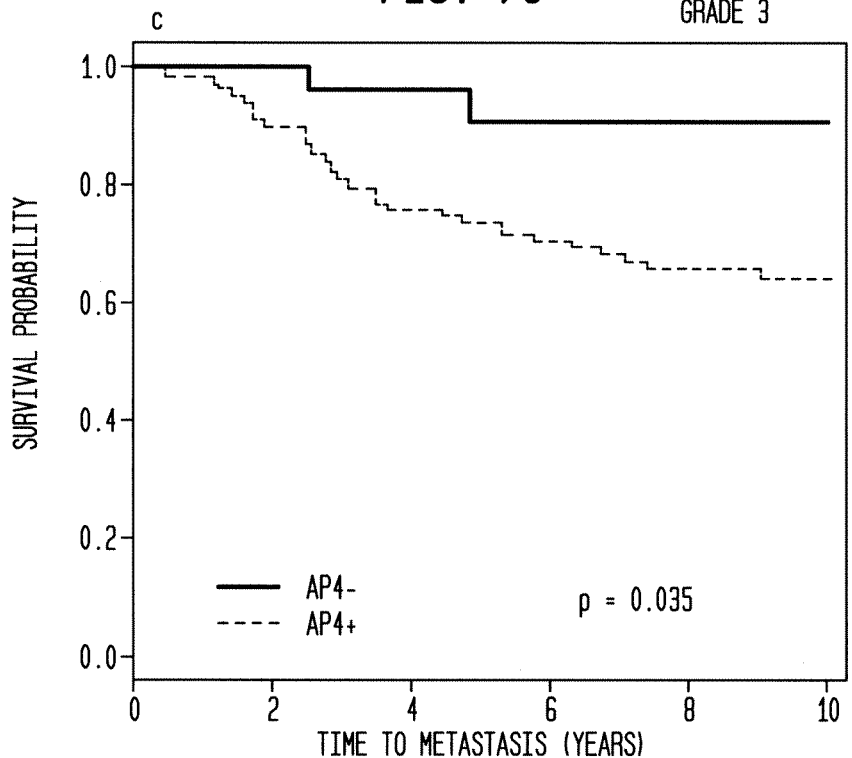
Figure 7D:
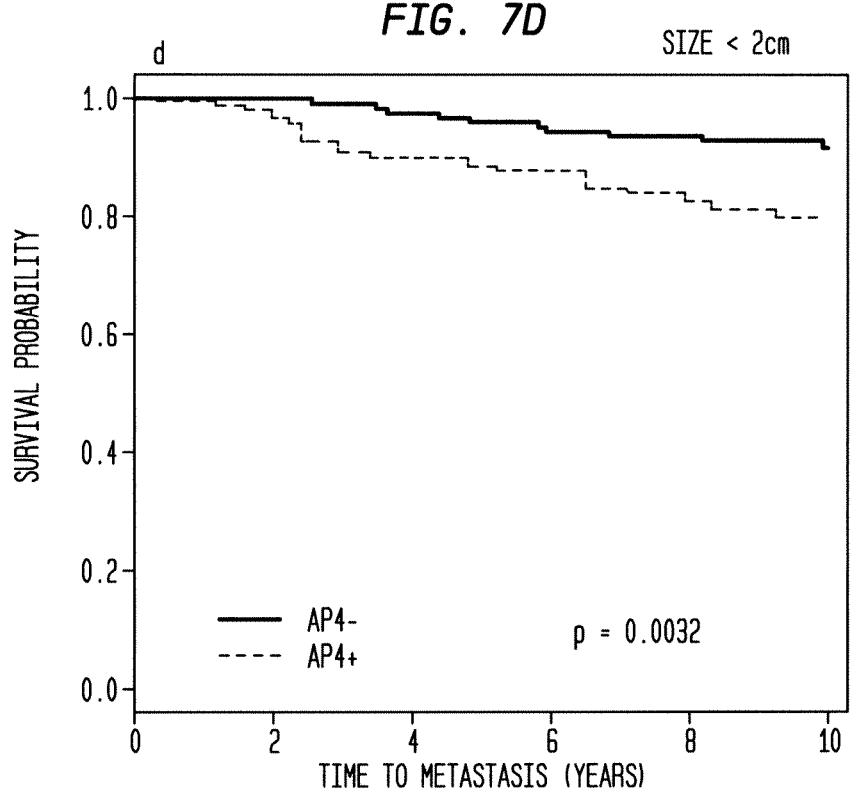

FIG. 7(a) denotes time to metastasis in breast cancer patients having a Grade 1 tumor, the patient's tumor having been assessed so as to classify it as AP 4+ or AP– according to the method described herein. Grade 1 tumor cells resemble normal cells, and tend to grow and multiply slowly. Grade 1 tumors are generally considered the least aggressive in behavior. FIG. 7(b) denotes time to metastasis in breast cancer patients having a Grade 2 tumor, the patient's tumor having been assessed so as to classify it as AP 4+ or AP– according to the method described herein; FIG. 7(c) denotes time to metastasis in breast cancer patients having a Grade 3 tumor, the patient's tumor having been assessed so as to classify it as AP 4+ or AP– according to the method described herein. Grade 3 tumors tend to grow rapidly and spread faster (metastasize) than tumors with a lower grade; FIG. 7(d) relates to a correlation of tumor size (<2) and time to metastasis, as between patients having a tumor of AP4+ or AP4– status; FIG. 7(e) relates to a correlation of tumor size to (≥2 cm) and time to metastasis, as between patients having a tumor of AP4+ or AP4– status; FIG. 7(f) relates to demonstrating time to metastasis in an L– (lymph node negative) population of breast cancer patients having been classified as either AD+ or AP4–; 7(g) relates to demonstrating time to metastasis in an L+ (lymph node positive) population of breast cancer patients having been classified as either AD+ or AP4–; 7(h) relates to demonstrating time to metastasis in an L– (lymph node negative) population of breast cancer patients having been classified as either AD+ or AP4–, these patients having a tumor size of <2 cm; FIG. 7(i) denotes time to metastasis in populations of ER+ breast cancer patients having been classified as AP4+ or AP4– status, and having been identified as having a Grade 2 tumor (size>2 cm).

DETAILED DESCRIPTION

The accelerated progression relapse test, developed here, utilizes genes that are not only connected to survival, but have expression patterns that define multiple subtypes, suggestive of distinct cellular states. Distinct expression patterns in two sets of patients suggest that different biological pathways may be active. In one embodiment, the AP test approach is analogous to the familiar separation of breast cancer tumors into ER+ and ER– groups. The difference between the two groups is more than a change along a continuum; different processes are active in the two groups. Moreover, there is significant evidence that cancer in humans progresses through a series of discrete steps reflecting genetic alterations (Hanahan 2000, Simpson 2005). Genes with expression patterns that divide patients into two subtypes, one of which is enriched with poor prognosis patients, may be the most direct markers of disease progression.

A method akin to clustering, known as mixture models, is used to identify genes that define distinct subtypes. Unsupervised clustering is a familiar method of deriving subtypes from microarray data of cancer samples (Sorlie 2001, Tibshirani 2002, Kapp 2006). These applications use measures of tens or hundreds of genes. According to one embodiment of the invention, samples are clustered using one gene at a time, much like the classification of samples as ER+ or ER–, ERBB2+ or ERBB2–, etc., utilizing only genes that define distinct subtypes in multiple patient cohorts. Such genes are called multi-state in this paper, and defined formally with mixture models in the Results section. Just as with ER status, for a multi-state probe p there is a threshold c such that the samples with expression values above c, denoted p+, form one component, and the samples with expression values below c, denoted p–, form the second component. FIG. 5 plots the density distributions in one cohort of the four multi-state probes used in ER+ AP relapse prognostic test. According to one embodiment of the invention, one component of a multi-state probe is approximately normally distributed and the other consists of a tail to the right or left.

The accelerated progression relapse test is developed using the multi-state probe methodology. The 4 probes for the AP4 are multi-state, and positively correlated with relapse, across independent cohorts. The good prognosis group in the accelerated progression test, AP4–, consists of the samples in the low expression component for each of the 4 probes. The remaining samples comprise the AP4+ group. In the union of 4 independent datasets, not used to derive the subtype, the hazard ratio for distant metastasis between AP4+ and AP4– is 3.76 (95% CI 2.16-6.56). The 10-year metastasis-free survival probability for the AP4– group is 0.89 (95% CI 0.85-0.93), making systemic chemotherapy of questionable benefit.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description of the present invention, "p" is defined as a microarray probe for a defined gene expression product.

Figure 1:
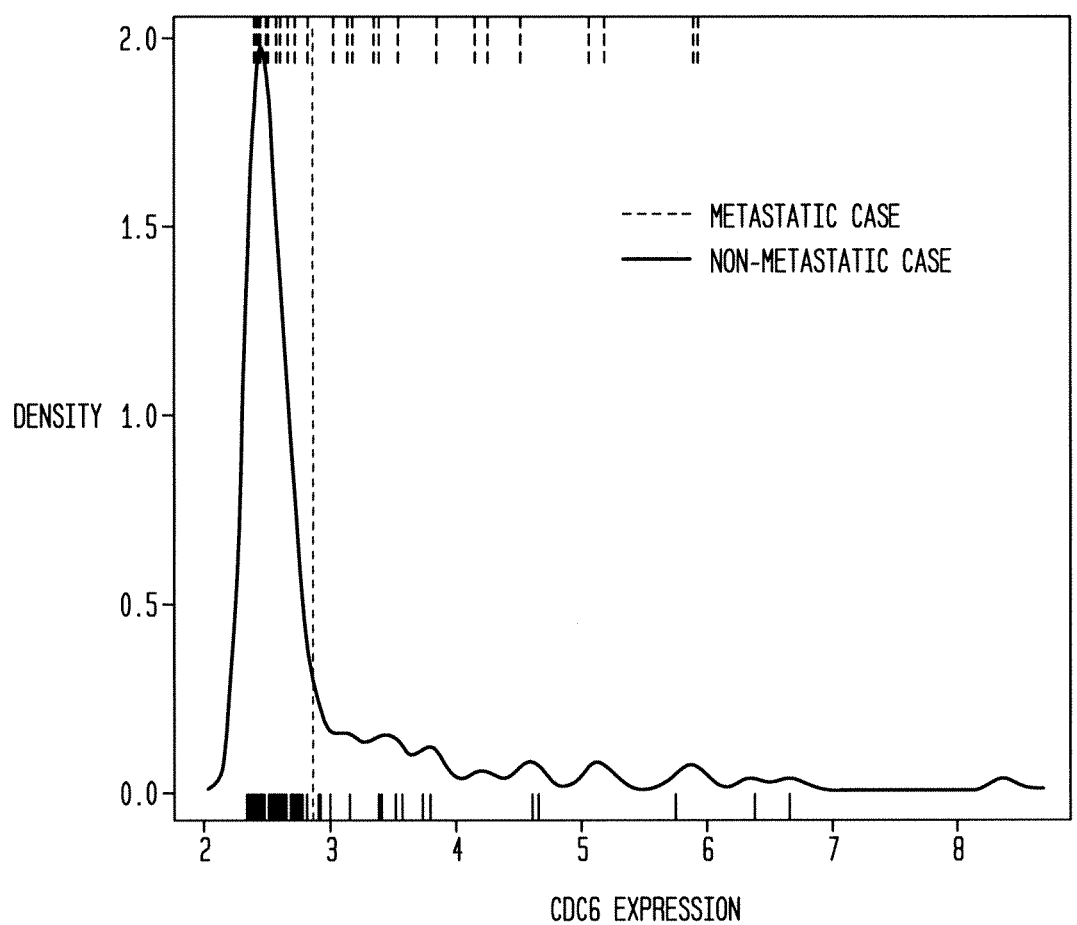
FIG. 1: According to one aspect of the invention, presents the density distribution of CDC6 divides into two components. The expression values are for the probe 203967_at in the ER+ samples in GSE7390, normalized with gcrma. Expression values for the metastatic cases are plotted with ticks at the top of the figure, and non-metastatic cases at the bottom. The density distribution shows a large normal component with low baseline expression, and a long right tail with elevated expression. The mixture model methods applied here calculate a cut point of 2.85 between the two components. While 47% of the samples in the right tail eventually metastasize, only 14% of the samples below the cutoff metastasize.

As used in the description of the present invention, a "multi-state gene" is defined as a gene capable of differential levels of expression within a patient population such that the expression levels of the gene in the patient population permits the patient population to be divided into at least two or more distribution groups based on density distribution according to statistical analysis of the expression level. For example, in one embodiment, the expression levels are divided into two groups based on a mixture model fit of expression levels of the gene of interest. For example, as shown in FIG. 1, the density distribution of expression levels of CDC6 in ER+ patient samples shows a large normal component with low baseline expression and a long right tail with elevated levels of CDC6 expression. Therefore, as exemplified herein, CDC6 is a multi-state gene. For example, in one embodiment, if the density distribution of gene expression for a particular gene of interest can be partitioned into at least two components, a large normal component of expression values below a threshold c, and a long right tail with expression values above c, the gene is a multi-state gene. Alternatively, in another embodiment, a gene is multi-state if the density distribution of gene expression for a particular gene of interest is partitioned into at least two components, a large normal component of expression values above a threshold c, and a long left tail with expression values below c.

AP (Accelerated Progression) status refers to the designation of a patient as having a high expression (+) or low expression (−) of a particular multi-state gene based on the expression levels for that patient for the particular multi-state gene of interest. In one embodiment of the invention, AP status with respect to breast cancer determined by four probes is either AP4+ or AP4−. For example, a patient's AP status is AP4+ when the gene expression level as measured by at least one of the four multi-state probes of interest is high (+). For example, a patient's AP status is AP4− when the gene expression level as measured by all four of the multi-state probes of interest is low (−).

Mixture Models. Given a numeric vector, the statistical method of finite mixture models partitions the vector into components, each of which is modeled by a different density distribution. The mixture models used to develop the Accelerate Progression Relapse Test described herein fit a pair of gaussian distributions to a vector. Such a model is described by a partition of the vector into components C1, C2, and a pair of gaussian distributions g1, g2 modeling the distributions of C1, C2, respectively. The modeling process simultaneously partitions the vector and selects the means, µ1, µ2 and standard deviations σ1, σ2 of the two gaussian distributions, with the goal of giving the best possible fit over all alternatives. The fitting algorithm actually produces, for each point and component, a posterior probability that the point is in that component. The point is assigned to the component whose associated posterior probability is maximal. For a point p that is well-classified in, say, component 1, the posterior probability that p is in C2 will be very small. For convenience, posterior probabilities below a threshold δ are reported as 0. Following Leisch 2004, we use δ=10−4. Points that are on the boundary between the two components will have posterior probability >δ for both components. The "isolatedness" of, e.g., component 1 is assessed by the ratio, r1=n1/m1, where n1 is the size of C1 and m1 is the number of elements with posterior probability of belonging to C1 greater than δ. Ratios are ≤1, with numbers close to 1 representing well-isolated components. Ratios are used to measure the ability of a mixture model fit to describe distinct states.

In most instances, the components defined by a fit of a pair of gaussian distributions consist of a pair of unbroken intervals. That is, there is a cutoff c so that one component consists of the values <c and the other component the values ≥c. In this way, mixture models can be used to calculate a threshold for dividing a vector into high and low components.

A standard measure of the quality of a mixture model fit is the likelihood, which is the product, over all points, of the maximal posterior probabilities. The likelihood can be used to decide, for example, if a fit with a pair of gaussian distributions is better than a fit with a single gaussian, or if a fit with Gamma distributions is better than a fit with gaussian distributions. Even better measures are AIC and BIC which adjust likelihood by the degrees of freedom. These measures play a part in defining the notion of a multi-state probe. According to one embodiment of this invention, mixture models were fit using the flexmix R package (Leisch 2004).

"Probe" means a polynucleotide molecule capable of hybridizing to a target polynucleotide molecule. For example, the probe could be DNA, cDNA, RNA, or mRNA. In one embodiment, a probe is fixed, for example, by a covalent bond, to a solid state apparatus such as a microarray. The probe and the target may hybridize, for example, under stringent, or moderately stringent conditions. A probe may be labeled, for example, with a fluorescent or radiolabel to permit identification. In one embodiment, a probe is of a sufficient number of base pairs such that it has the requisite identity to bind uniquely with the target and not with other polynucleotide sequences such that the binding between the target and the probe provides a statistically significant level of accurate identification of the target molecule. In one embodiment, a probe's ability to bind a target is correlated to a statically significant prognostic indicator of a defined disease state as determinable using an identified panel of genes of interest. In one embodiment, the target is mRNA and the probe is a complementary piece of DNA or cDNA. In another embodiment, the target is cDNA or DNA and the probe is a complementary piece of mRNA. In another embodiment, the target is cDNA or DNA and the probe is a complementary piece of DNA.

By the term "multi-state probe" is meant, in one embodiment, a probe capable of hybridizing with a target polynucleotide molecule encoding a multi-state gene. In another embodiment, a "multi-state probe" means a probe capable of hybridizing with a target polynucleotide molecule encoding a relevant portion or fragment of a multi-state gene. For example, the target polynucleotide molecule may be mRNA. In one embodiment, a multi-state probe is fixed to a solid state apparatus such as a microarray by, for example, a covalent bond. In one embodiment, hybridization between the probe and the target occurs under stringent conditions.

The term "hybridize" or "hybridizing" or "hybridization" refers to the formation of double stranded nucleic acid molecule between complementary sequences by way of Watson-Crick base-pairing. Hybridization can occur at various levels of stringency according to the invention. "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C. "Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37 50° C. The skilled artisan will recognize how to adjust the temperature, ionic strength, etc. as necessary to accommodate factors such as probe length and the like.

The term "microarray" refers to an ordered arrangement of hybridizable array elements, preferably polynucleotide probes, on a substrate.

The terms "differentially expressed gene," "differential gene expression," and their synonyms, which are used interchangeably, refer to a gene whose expression is activated to a higher or lower level in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or between various stages of disease development in a diseased subject.

The term "over-expression" with regard to an RNA transcript is used to refer to the level of the transcript determined by normalization to the level of reference mRNAs, which might be all measured transcripts in the specimen or a particular reference set of mRNAs.

The term "prognosis" is used herein to refer to the prediction of the likelihood of cancer-attributable death or progression, including recurrence, metastatic spread, and drug resistance, of a neoplastic disease, such as breast cancer.

The term "prediction" is used herein to refer to the likelihood that a patient will respond either favorably or unfavorably to a drug or set of drugs, and also the extent of those responses, or that a patient will survive, following surgical removal or the primary tumor and/or chemotherapy for a certain period of time without cancer recurrence. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, chemotherapy with a given drug or drug combination, and/or radiation therapy, or whether long-term survival of the patient, following surgery and/or termination of chemotherapy or other treatment modalities is likely.

The term "long-term" survival is used herein to refer to survival for at least 3 years according to one embodiment, at least 8 years according to a more preferred embodiment, and at least 10 years according to a most preferred embodiment, following surgery or other treatment.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, breast cancer, ovarian cancer, colon cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

In the context of the present invention, reference to "at least one," "at least two," "at least five," etc. of the genes listed in any particular gene set means any one or any and all combinations of the genes listed.

The term "node negative" cancer, such as "node negative" breast cancer, is used herein to refer to cancer that has not spread to the lymph nodes.

The term "gcrma" refers to a method know to those of skill in the art whereby raw data obtained from an Affymetrix® microarray is normalized.

"Normalization" refers to statistical normalization. For example, according to one embodiment, a normalization algorithm is the process that translates the raw data for a set of microarrays into measure of concentration in each sample. A survey of methods for normalization is found in Gentleman et al. (Bibliography Ref. No. 41). For example, a microarray chip assesses the amount of mRNA in a sample for each of tens of thousands of genes. The total amount of mRNA depends both on how large the sample is and how aggressively the gene is being expressed. To compare the relative aggressiveness of a gene across multiple samples requires establishing a common baseline across the samples. Normalization allows one, for example, to measure concentrations of mRNA rather than merely raw amounts of mRNA.

"Biologically homogeneous" refers to the distribution of an identifiable protein, nucleic acid, gene or genes, the expression product(s) of those genes, or any other biologically informative molecule such as a nucleic acid (DNA, RNA, mRNA, iRNA, cDNA etc.), protein, metabolic byproduct, enzyme, mineral etc. of interest that provides a statically significant identifiable population or populations that maybe correlated with an identifiable disease state of interest.

"Low expression," or "low expression level(s)," "relatively low expression," or "lower expression level(s)" and synonyms thereof, according to one embodiment of the invention, refers to expression levels, that based on a mixture model fit of density distribution of expression levels for a particular multi-state gene of interest falls below a threshold c, whereas "high expression," "relatively high," "high expression level(s)" or "higher expression level(s)" refers to expression levels failing above a threshold c in the density distribution. The threshold c is the value that separates the two components or modes of the mixture model fit.

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", 2.sup.nd edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4.sup.th edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

EXAMPLE 1

The present example is provided to define the statistical tools and models and data sets employed is deriving the present methods.

The microarray datasets used here were obtained from the Gene Expression Omnibus (http://www.ncbi.nlm.nih.gov/geo/), specifically, GSE4922, GSE6532, GSE7390, GSE9195, GSE11121. Two independent cohorts were obtained from GSE6532, for a total of 6 cohorts, with 813 estrogen receptor+ (ER+) samples. None of the patients received adjuvant chemotherapy. A summary of the clinical traits of the patients is found in Table 2 below. Expression values were computed from raw data with gcrma[26]. The language R (http://www.r-project.org/) was used for all statistical analyses. Mixture models were fit using the flexmix[27] R package. The R package survival was used for all survival models. The proportional hazard condition was verified with the cox.zph function. A Cox proportional hazard model (CPH) was considered statistically significant if the p-value of the logrank score is <0.05.

necessary, the left tail of v is trimmed so that the resulting two components consist of the values below and above a cutoff c. The mixture model associates to each component a ratio (between 0 and 1) that reflects the quality of the component's fit to a Gaussian distribution. A higher ratio denotes a better fit. Given a large set of probes whose increased expression is positively correlated with relapse, let r be the median of the ratios for the low components.

A probe is defined to be multi-state in S if the maximum ratio of its mixture model is above r. For probes negatively correlated with relapse, the roles of low and high components are reversed. Inspection of the density plots of probes supports this formalization of the concept of a probe with two components.

EXAMPLE 2

Methods (a) Patient Cohorts and Data Analysis

Estrogen receptor status was determined here from expression values for a probe for ESR1. In all cohorts, the survival endpoint used was distant metastasis, except in GSE4922, in which it was any recurrence. All survival data was censored to 10 years so as not to distort the data due to different study lengths. In each cohort, the mRNA was extracted from primary tumors and hybridized to an array from the Affymetrix GeneChip platform hgu133a or hgu133plus2.

(b) GCRMA is Used to Calculate Expression Values

Expression values are computed from the CEL files with GCRMA (Wu 2004). Many of the genes central to proliferation are unexpressed or expressed at a low baseline level in normal tissue. Given the prominent role played by proliferation in breast cancer progression, it is important to measure low concentration mRNA levels as precisely as possible. It was shown in (Irizarry 2006) with spike-in data that GCRMA has superior accuracy and precision to other methods in measuring low concentration mRNA. The effect on the AP4 model of using MASS instead of GCRMA is described in the Discussion section.

Note that GCRMA is applied separately to each of the 6 microarray datasets. Expression values in different datasets are never compared to each other. This allows us to include in the study datasets based on both hgu133a and hgu133plus2. A binary variable for each probe in the AP4 model is calculated as a step in forming the AP4 partition in a dataset. Whether a sample has a value 0 or 1 is based only on the probe's expres-

TABLE 2

Detailed information about the clinical traits of the patients can be found in the references supplied at the Gene Expression Omnibus.

|  | Uppsala | Transbig | Guys 1 | Oxford | Guys 2 | Mainz |
|---|---|---|---|---|---|---|
| GEO | GSE4922 | GSE7390 | GSE6532 | GSE6532 | GSE9195 | GSE11121 |
| array | hgu133a | hgu133a | hgu133plus2 | hgu133a | hgu133plus2 | hgu133a |
| # samples | 249 | 198 | 87 | 178 | 77 | 200 |
| # ER+ | 200 | 138 | 85 | 144 | 77 | 169 |
| LN+/−/? on ER+ | 62/132/6 | 0/138/0 | 56/29/0 | 36/102/6 | 36/41/0 | 0/169/0 |
| Tamox. | ? | ? | 85 | 105 | 77 | ? |

The Oxford cohort is the union of the OXFU and OFXT series in GSE6532. This table illustrates varying lymph-node status and treatment status for tamoxifen across these cohorts. These are particularly relevant given the restriction of Oncotype DX assay and Mammaprint assay to node negative patients.

Consider the expression vector v of a probe whose increased expression causes greater risk of recurrence in a cohort S. The multi-state status of v is determined by first fitting v to a mixture model with two Gaussian components. If sion values within the dataset. In studying properties of the AP4 model we do merge the datasets of binary variables. This allows us to reference, e.g., one large validation dataset that is the union of four cohorts.

(c) Multi-State Probes are Defined with Mixture Models

Distinct gene expression patterns are used according to the invention to model distinct biological states. At a basic level, mixture models can be fit to expression vectors to identify these different states. However, the natural variation in expression patterns makes it a challenge to decide which fits to multiple distributions represent distinct states and which are simply anomalies in the data. The fact that most microarray databases contain fewer than 200 samples accentuates the problem. In a preliminary study it was determined that, ranging over a large set of probes in one microarray database, for all but a few probes, a fit with a pair of gaussian distributions has higher likelihood than a fit with a single distribution (either gaussian or Gamma). A more stringent measure than likelihood is needed to separate those patterns that represent distinct states from noise.

Let x denote the expression vector of a gene such that increased expression is positively correlated with relapse in a cohort of ER+ breast cancer patients. Suppose that a fit to a pair of gaussian distributions produces two components, consisting of the values above a threshold c and the values below c. The high component will be enriched with metastatic cases. For a gene that significantly influences metastasis, many of the samples in the high component will be metastatic. In a representative cohort only about 25% of the patients eventually metastasize, so the high component is likely much smaller than the low good prognosis component. Instead of appearing as a pair of components of equal size, it is modeled by a large normal component and a right tail of elevated values. The degree of separation of the tail from the low component is a measure of the quality of this fit. Referring to the parameters described above, this suggests that a high value for the ratio of the low component indicates a gene with distinct states. For a gene y that is negatively correlated with relapse, the high component is the good prognosis group and the low component is enriched with metastatic cases. In analogy with x, the ratio of the high component of y measures the quality of this fit. In either case, the ratio of the good prognosis component is the important parameter.

Given a microarray database S, let Y be a large set of probes that are correlated with relapse. For each probe p in Y, fit a pair of gaussian distributions to the expression vector for p in S, and let rp be the ratio of the good prognosis component. Let r0 be the median of rp, for p in Y. A probe p in Y is multi-state in S if rp>r0.

The density distributions of the four probes in AP4 in the TRANSBIG+ cohort are plotted in FIG. 1, along with the cutoffs between high and low components and indicators for metastatic cases.

An adjustment to the mixture model process is required for a probe whose distribution can be modeled with a pair of gaussian distributions in multiple ways, or when the components are broken intervals. This occurs when, as in FIG. 1(c), the optimal fit is with 3 gaussian components instead of 2. However, routinely fitting expression vectors with more than 2 gaussian distributions risks over fitting the data. It is rare for the 3 component fit to be optimal across multiple cohorts. Instead, for a vector positively correlated with relapse we remove from the vector the lowest 10% of values prior to fitting with a pair of gaussian distributions. For a gene negatively correlated with relapse we trim the highest 10% of values. This correction is necessary for fewer than 5% of the probes in this study and does not effect the cutoff between components for other probes.

The parameters for the pair of gaussian distributions can be used to illustrate the quality of the fit for multi-state probes in specific datasets. Let Y be the 100 most significant probes in the UPPS+ cohort, as described below in the derivation of AP4. The median ratio of good prognosis components for this set is 0.89. Let x be the expression vector of a multi-state probe positively correlated with relapse, gL, gH the gaussian distributions of the low and high components, $\mu L$, $\mu H$ and $\sigma L$, $\sigma H$ the means and standard deviations of gL, gH, respectively, and c the cutoff between the low and high components. We find empirically, that for any such x that is multi-state, $\mu H - \mu L > 5\sigma L$ and $c - \mu L > 2.8\sigma L$. That is, all elements of the high component are above the 0.997 quantile of gL. This shows a high degree of separation between the components.

It is worth noting that, in some instances, a fit with a pair of Gamma distributions has a higher likelihood than a fit with gaussian distributions. However, checking the multi-state probes in one cohort in the study, the components defined by Gamma distributions and gaussian distributions are exactly the same for half of the probes and never differ by more than 2%. Thus, according to one embodiment, the method uses only with the simpler gaussian distributions.

(d) Survival Models

Reflecting the position that the +/− status of a multi-state probe is as informative as the raw expression values, multi-state probes are represented in survival models as binary variables: 0 for the good prognosis component, and 1 for the other. For X a multi-state probe or corresponding binary variable, gd(X) denotes the good prognosis group of samples. For a probe positively correlated with relapse, gd(X) is the low expression component.

Survival models using multiple multi-state probes are defined to focus attention on the good prognosis samples. The partition of samples generated by a set of multi-state probes $X_1, \ldots, X_n$ distinguishes the samples in $gd(X_i)$, for all i, from the rest. Identifying the $X_i$ with binary variables, this partition is defined by the binary variable Y that is 0 when every $X_i$ is 0, and 1 otherwise; Y is formally denoted $X_1^* \ldots *X_n$. The survival model generated by $X_1, \ldots, X_n$ is a model whose sole variable is the binary variable $X_1^* \ldots *X_n$. For Y the * product of multi-state probes, gd(Y) is the set of samples on which Y is 0. Gradations of risk in the poor prognosis group that may be defined by multiple probes are not part of this study.

Given a set P of multi-state probes and a sample cohort S, an optimal survival model derived from P is defined by a binary variable Y such that (1) $Y = X_1^* \ldots *X_n$, for some $X_1, \ldots, X_n$ in P, (2) on gd(Y) no CPH using a single Z in P is significant, and (3) no variable Y' that is the * product of a proper subset of $X_1, \ldots, X_n$ satisfies (2). Less formally, gd(Y) is a maximal intersection of good prognosis sets defined with elements of P that cannot be significantly improved by intersecting with a further element of P.

(e) Derivation of the AP4 Model

The AP4 model is derived with the ER+ samples in two cohorts as training sets, GSE4922 (denoted UPPS+) and GSE7390 (TRANSBIG+). An initial set of 100 significant probes is defined as follows. Working in UPPS+, 100 training sets are selected, each containing ⅔ of the samples that relapse and ⅔ of the samples that do not relapse. For each training set and each probe p, a CPH is computed using as its sole variable the expression values of the probe in the training set. For each training set, the 100 most significant probes, as measured by the logrank score p-value, are selected. Finally, let Y be the 100 probes that occur most frequently in the top 100 probes for these training sets.

EXAMPLE 3

Molecular Probes

A set of probes to serve as candidates for inclusion in the model is selected as follows. Let $Y_{up}$ be the probes in Y that are positively correlated with relapse. Let $P_{up}$ be the probes p in $Y_{up}$ such that (1) p is multi-state in both UPPS+ and TRANSBIG+, and (2) the binary variable representing p is significant in a CPH in UPPS+ and TRANSBIG+. A set $P_{dn}$ of probes negatively correlated with relapse is derived correspondingly. The set of candidate probes P is the union of $P_{up}$ and $P_{dn}$. Executing this procedure yields a set of 16 probes.

An optimal survival model derived from P in UPPS+ is generated by CDT1 (209832_s_at), SPAG5 (203145_at), CDC6 (203967_at), and SNRPA1 (216977_x_at). In TRANSBIG+ an optimal survival model derived from P is generated by MKI67 (212020_s_at), SPAG5 (203145_at), PLK1 (202240_at), SNRPA1 (216977_x_at), and MKI67 (212022_s_at). In both cases the probes are all positively correlated with relapse, hence the good prognosis group for any probe is the low expression component. As the initial model, called AP7, we choose the one generated by the 7 probes obtained from either cohort. This ensures that samples in AP7− in UPPS+ and TRANSBIG+ have good prognosis. While the process identifies AP7, models generated by fewer of these probes perform as well in the 6 cohorts in this study. One of these tests is AP4. Note that some continuous expression vectors for probes in Y are significant in a CPH in AP7− in UPPS+ and in TRANSBIG+, but no probe is significant in both cohorts.

Monte Carlo cross validation of the cutoffs. Given a microarray dataset for a cohort S and a subset of samples $S_0$ balanced for relapse, thresholds are determined for the 4 probes in AP4 using the expression vectors in $S_0$. A sample not in $S_0$ is classified as AP4+ or AP4− using the cutoffs defined in $S_0$ and this status is compared to that calculated using all of S. To $S_0$ we associate the fraction of misclassified samples. The estimated error rate due to instability of the cutoffs is the mean value over a large set of subsets, $S_0$. In this study we use 1,000 subsets.

EXAMPLE 4

Accelerated Progression Relapse Test

Many breast cancer patients will remain relapse-free even without chemotherapy; however, accepted clinico-pathological variables are unreliable indicators of prognosis. The novel accelerated progression relapse test of the present invention separates patients with good prognosis from those with a poor prognosis on the basis of an assay that monitors the relative expression levels of four (4) genes. It offers a test for relapse with power comparable to, and in some cases superior to, others on the market at a fraction of the cost.

The algorithm reported here can be applied to any cancer subtype that is biologically homogeneous. For example, such cancer subtypes include colon cancer, lung cancer, prostate cancer, ovarian cancer, pancreatic cancer, esophageal cancer, and stomach cancer.

Technical description. The accelerated progression (AP) relapse test divides estrogen-receptor positive (ER+) breast cancer patients into two groups based on the expression values of four genes. A gene's expression level may be assessed using microarray technology, for example, Affymetrix® microarrays or immunohistochemical staining techniques.

With respect to microarray technology, messenger RNA is extracted from a breast tumor sample and hybridized to probes for the genes of interest present on the microarray chip, resulting in a numerical measure for each feature (gene) on the microarray. The resulting information is collected to form a microarray dataset containing an expression level for each gene and each patient in the cohort. The datasets analyzed were generated using Affymetrix hgu133a or hgu133plus2 arrays and were normalized with gcrma.

A novel feature of this test is the focus on genes that are both connected to disease progression and have expression patterns that indicate multiple cellular states. The AP relapse test of the invention, when applied to ER+ breast cancer, is derived from the following collection of multi-state probes (genes) shown in Table 3.

TABLE 3

| Affymetrix ® Probe ID | GeneID | GenBank Accession No. | Symbol | UNIGENE Code | Name |
|---|---|---|---|---|---|
| 212020_s_at | 4288 | AU152107 | MKI67 | Hs.689823 | antigen identified by monoclonal antibody Ki-67 |
| 212022_s_at | 4288 | BF001806 | MKI67 | Hs.689823 | antigen identified by monoclonal antibody Ki-67 |
| 220651_s_at | 55388 | NM_018518 | MCM10 | Hs.198363 | minichromosome maintenance complex component 10 |
| 203967_at | 990 | U77949 | CDC6 | Hs.405958 | cell division cycle 6 homolog (*S. cerevisiae*) |
| 209832_s_at | 81620 | AF321125 | CDT1 | Hs.122908 | chromatin licensing and DNA replication factor 1 |
| 203145_at | 10615 | NM_006461 | SPAG5 | Hs.514033 | sperm associated antigen 5 |
| 216977_x_at | 6627 | AJ130972 | SNRPA1 | Hs.528763 | small nuclear ribonucleoprotein polypeptide A' |
| 202240_at | 5347 | NM_005030 | PLK1 | Hs.592049 | polo-like kinase 1 (*Drosophila*) |
| 204126_s_at | 8318 | NM_003504 | CDC45L | Hs.474217 | CDC45 cell division cycle 45-like (*S. cerevisiae*) |
| 208103_s_at | 81611 | NM_030920 | ANP32E | Hs.656466 | Acidi (leucine-rich) nuclear phosphoprotein 32 family, member E |
| 204817_at | 9700 | NM_012291 | ESPL1 | Hs.153479 | Extra spindle pole bodies homolog 1 (*S. cerevisiae*) |

For a probe p, a sample is p+ if it lies in the high expression component of p; it is p− if it is below the cutoff or threshold.

Definition of Accelerated Progression Subtype. Let X be any collection of the above probes that contains both probes for MKI67 and the probe for CDC6. Define a sample to be accelerated progression positive (X+) if the sample is p+ for some p in X. The sample is X− otherwise. According to one embodiment of the invention, the accelerated progression test is defined with AP4=the probes for MKI67 (2 probes), CDC6 (1 probe) and SPAG5 (1 probe). According to the AP4 embodiment, if at least one of the four probes is high expression, then the patient's AP status is AP4+. If all the four probes are low expression, then the patient's AP status is AP4−.

Figure 2:
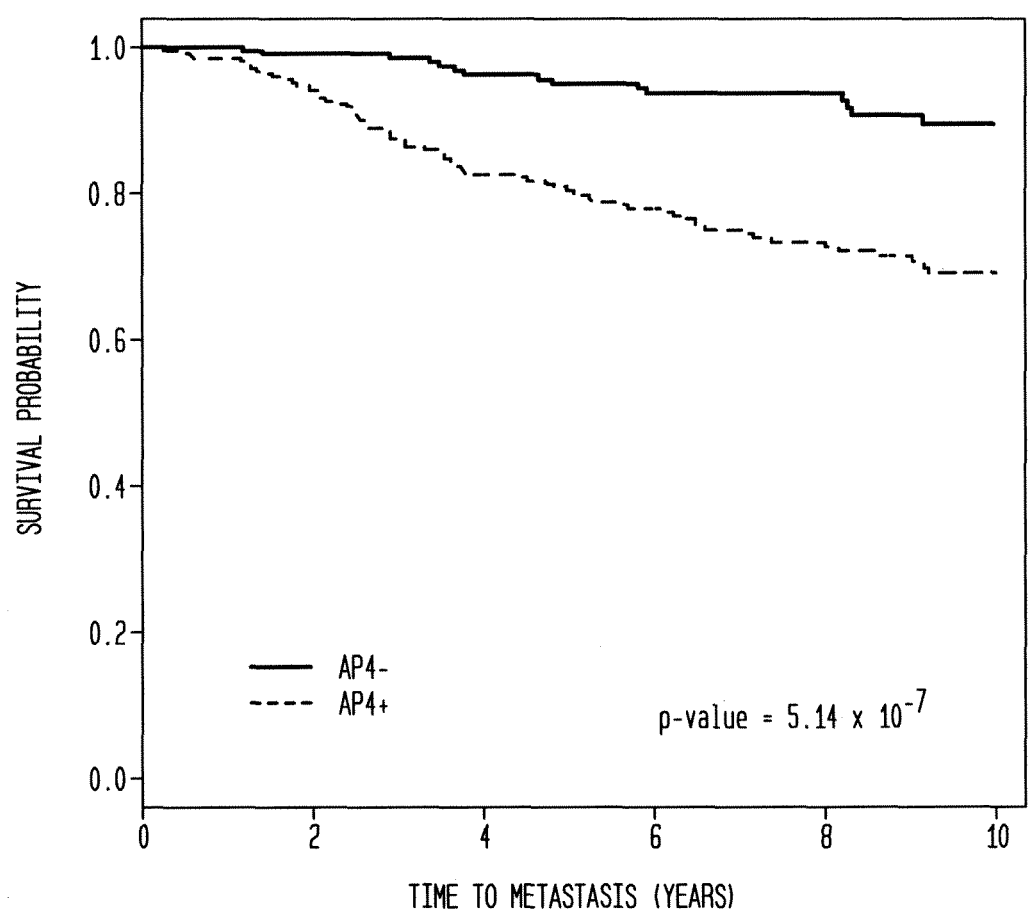
FIG. 2: According to one aspect of the invention, presents the Kaplan-Meier survival plot for AP4+/− in the validation set of ER+ samples from GSE6532, GSE9195, and GSE11121. The 5 and 10-year metastasis-free survival probabilities for the AP4− group are 0.95 (95% CI 0.92-0.98) and 0.90 (95% CI 0.85-0.95), respectively. The corresponding probabilities for the AP4+ group are 0.81 (95% CI 0.76-0.86) and 0.69 (95% CI 0.63-0.76). The hazard ratio between AP4+ and AP4− is 3.76 (95% CI 2.16-6.56).
Figure 3A:
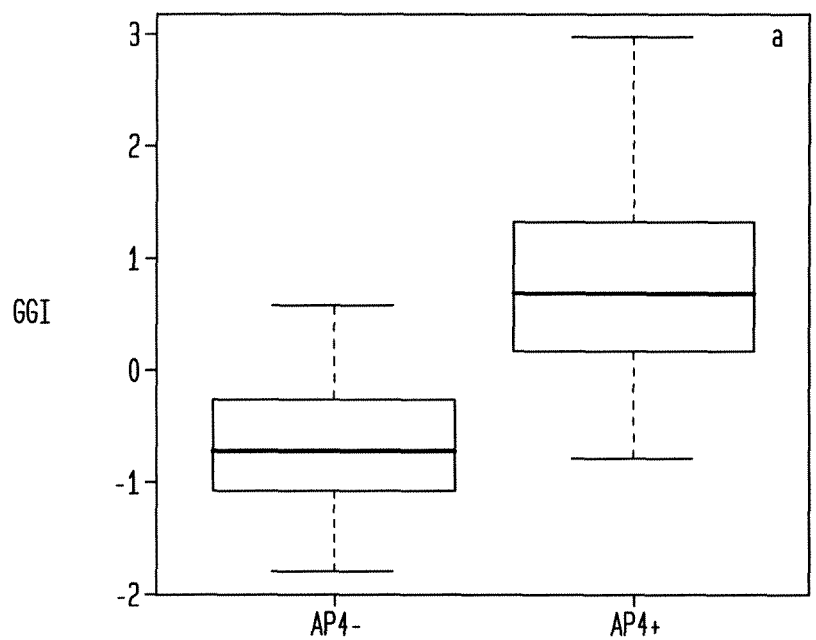
FIG. 3: According to one aspect of the invention, presents the distribution of GGI (3a) and TOP2A (3b) across the AP4+/− groups suggests that chemo-sensitive tumors are AP4+. The plots were generated with the GSE7390 cohort. Both of the probes representing TOP2A in the hgu133a platform yield similar plots.
Figure 3B:
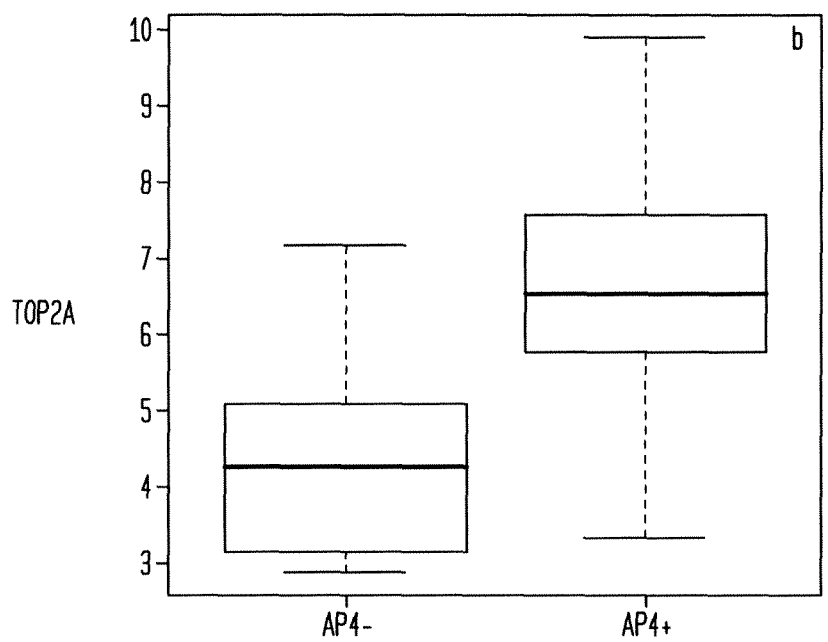
Figure 4A:
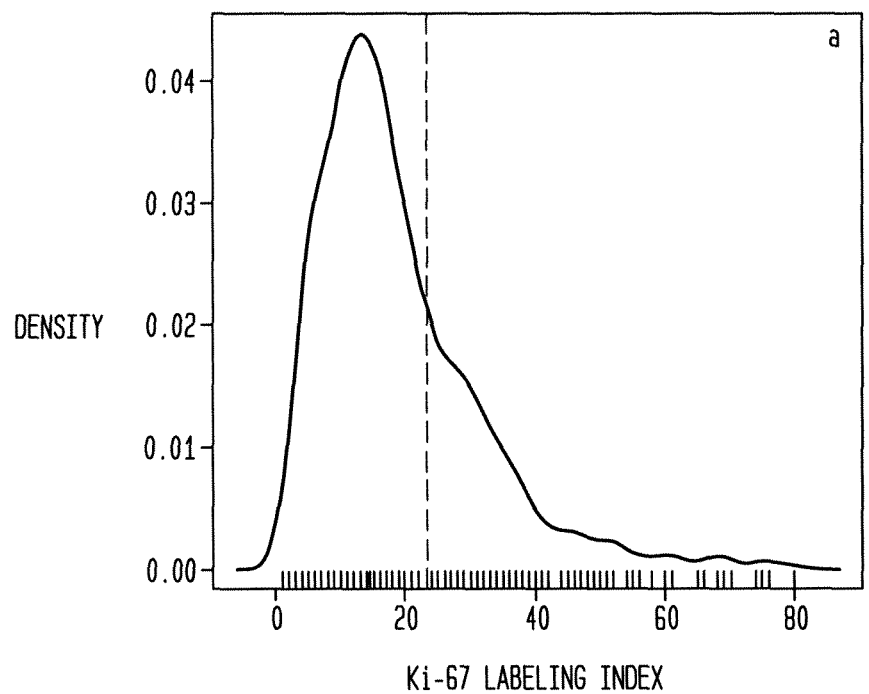
FIG. 4: According to one aspect of the invention, presents the Ki-67 labeling indices and the expression values for the MKI67 gene measured in a microarray dataset have similar distributions. (4a) This plots the density distribution for labeling indices from the ER+ samples in Trial IX of the International Breast Cancer Study Group[22]. The multi-state probe methodology defines a cutoff of 23% between the low and high components. (4b) This is the density distribution for MKI67 (212022_s_at) in the GSE7390 cohort, with the cutoff of 4.85.
Figure 4B:
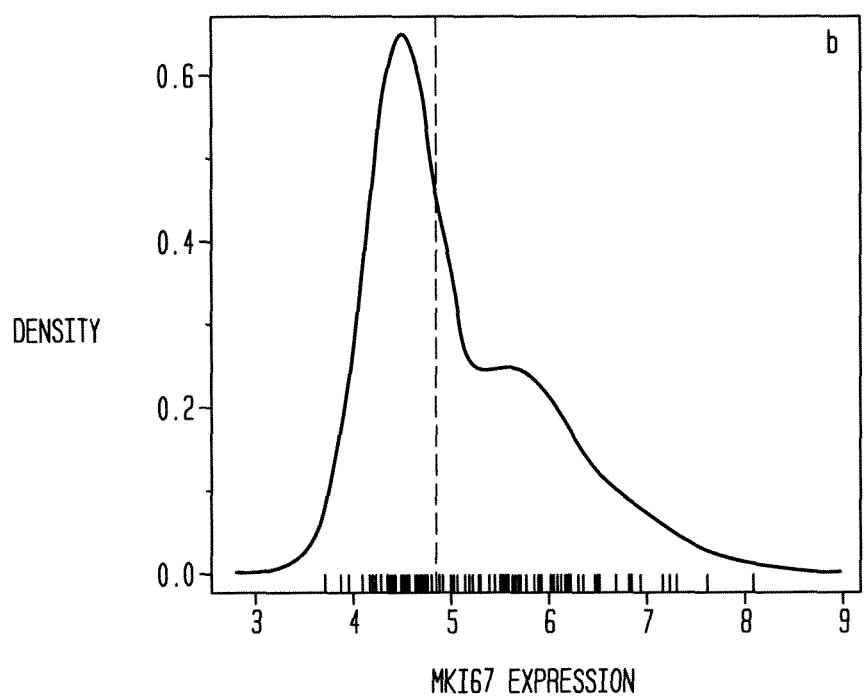
Figure 5A:
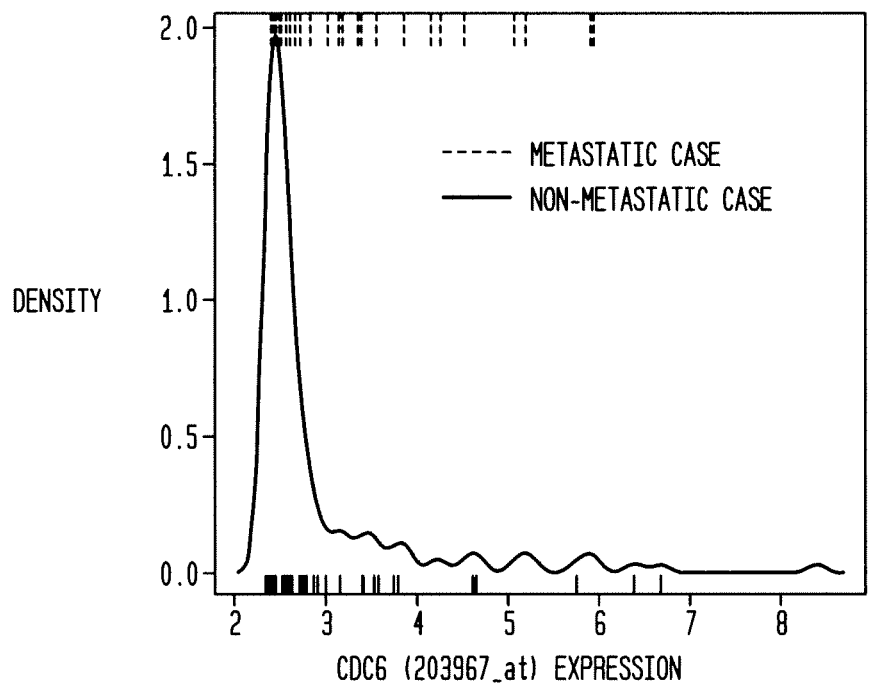
FIG. 5: According to one aspect of the invention, presents the density distributions of the probes in AP4 and shows how they divide into high and low components. The expression values are for the four probes from the ER+ samples in the TRANSBIG cohort. The density distribution of each probe shows a large component with low baseline expression and small standard deviation, and a long right tail with elevated expression. The mixture model method applied here calculates cutoffs between the two components, indicated by the dotted vertical lines. In each case, the high component is significantly enriched with metastatic cases. The ratios of the low components are: CDC6, 0.95; MKI67 (212022_s_at), 0.85; MKI67 (212020_s_at), 0.89; SPAG5, 0.85. The ratio cutoff for being considered a multi-state probe in this cohort is 0.83. Metastatic cases in each of panels a-d are shown along the top horizontal axis and non-metastatic cases are shown along the bottom horizontal axis.
Figure 5B:
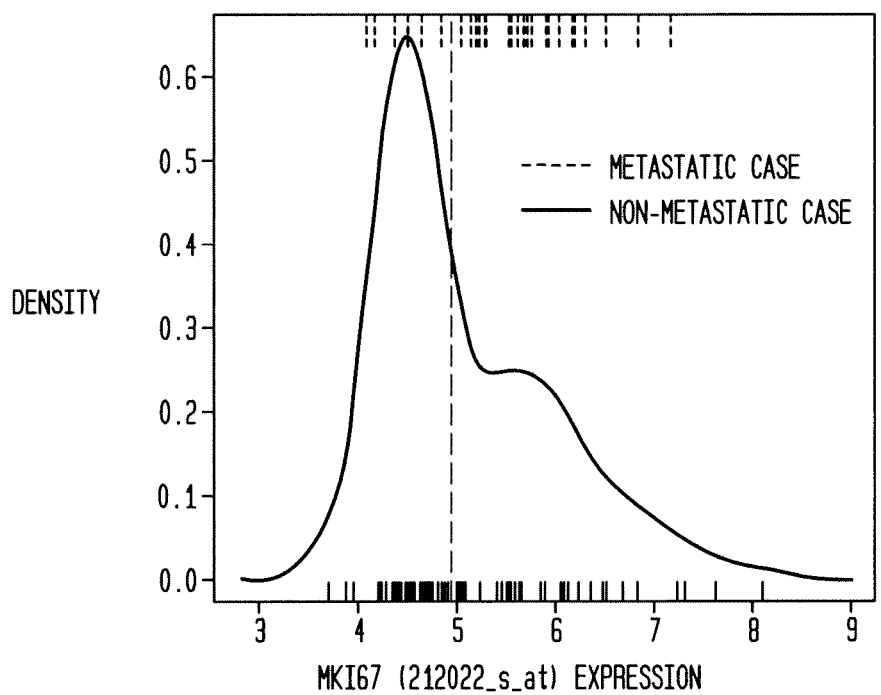
Figure 5C:
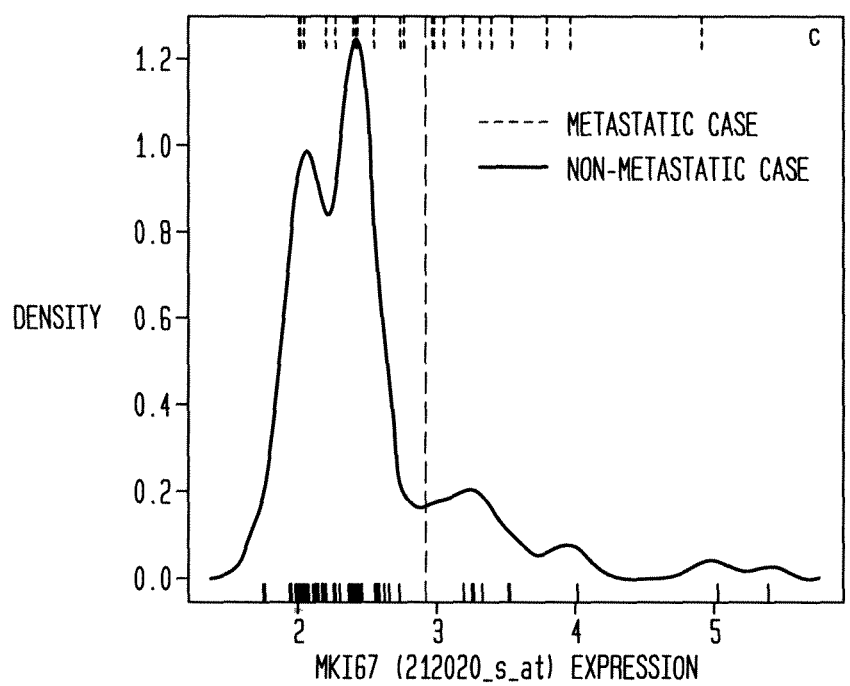
Figure 5D:
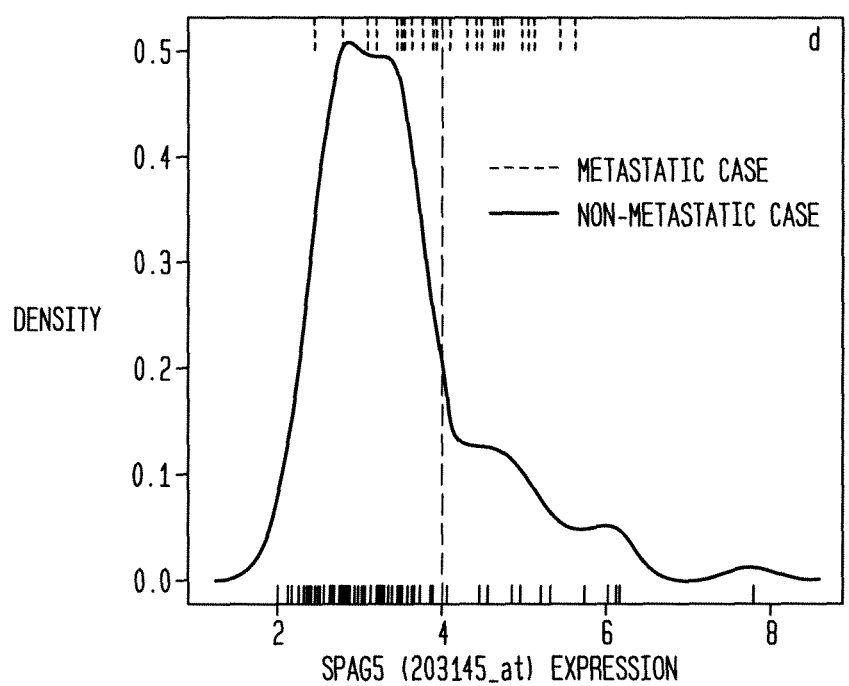
Figure 6A:
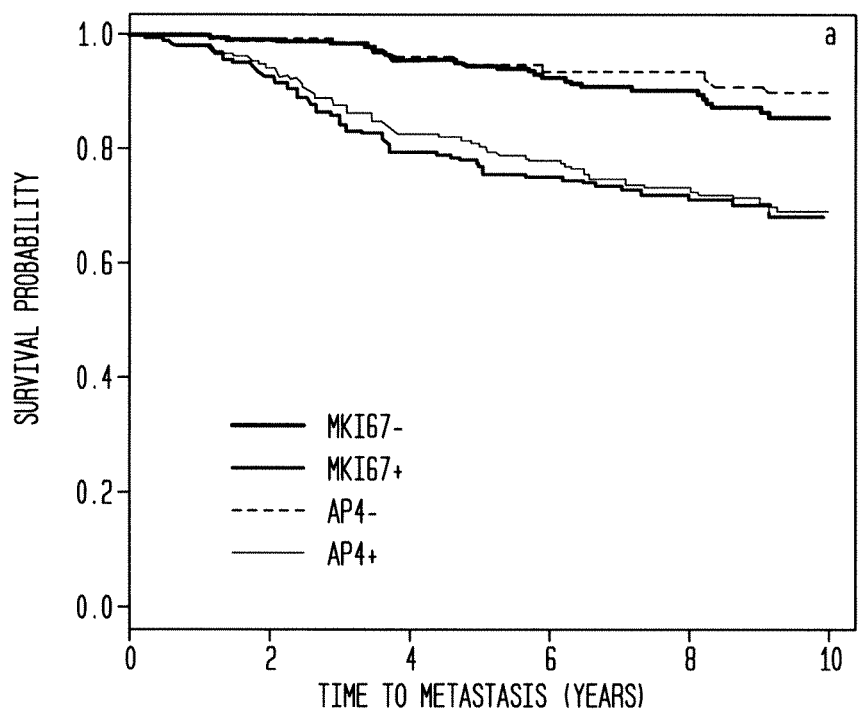
FIG. 6. According to one aspect of the invention presents Kaplan-Meier survival plots for the individual genes in AP4. The partition defined by each of the AP4 genes individually is a significant predictor of metastasis, however each is less significant than AP4. In (a), MKI67 denotes the probe 212022_s_at and in (c), MKI67.2 denotes the probe 212020_s_at. The sample set is the same set is the union of the ER+ samples in OXFD, GUYT, MZ and GUYT2. The hazard ratios, with 95% confidence intervals, for these genes are: MKI67, 2.90 (1.84-4.57); CDC6, 2.47 (1.62-3.75); MKI67.2, 1.84 (1.20-2.82); SPAG5, 2.91 (1.92-4.43). These are significantly smaller than the hazard ratio of 3.76 for AP4.
Figure 6B:
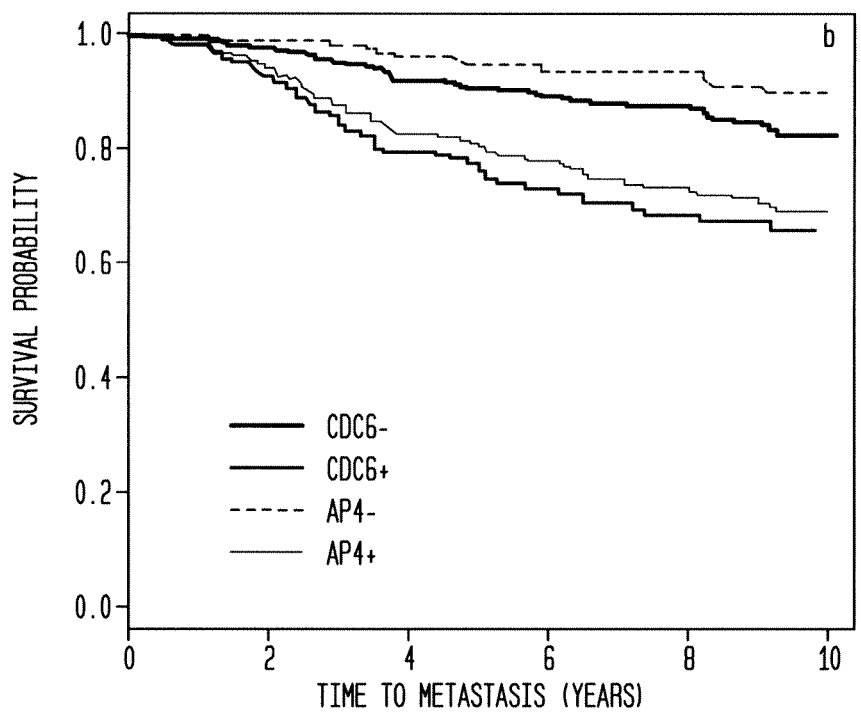
Figure 6C:
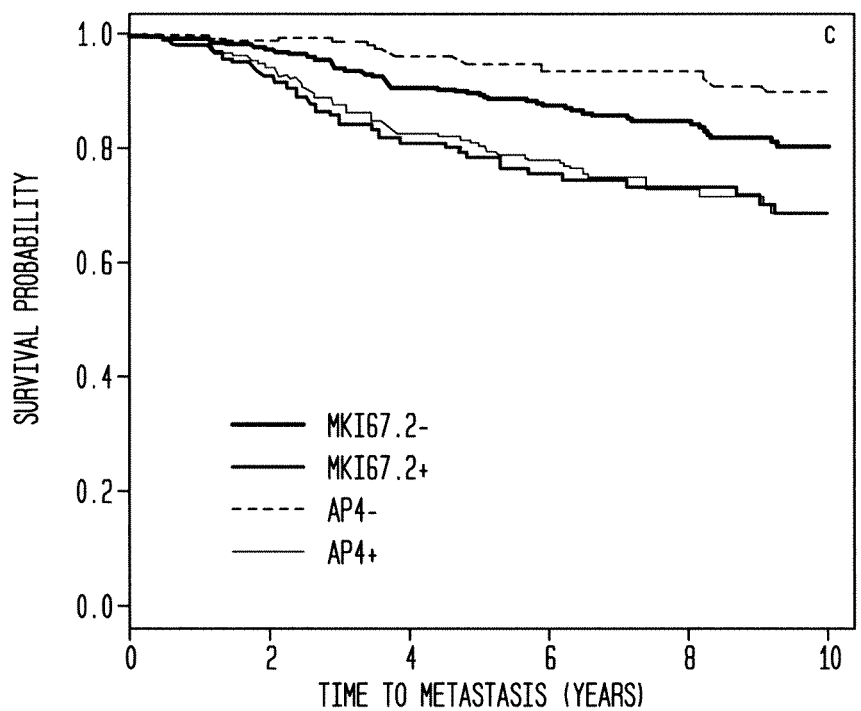
Figure 6D:
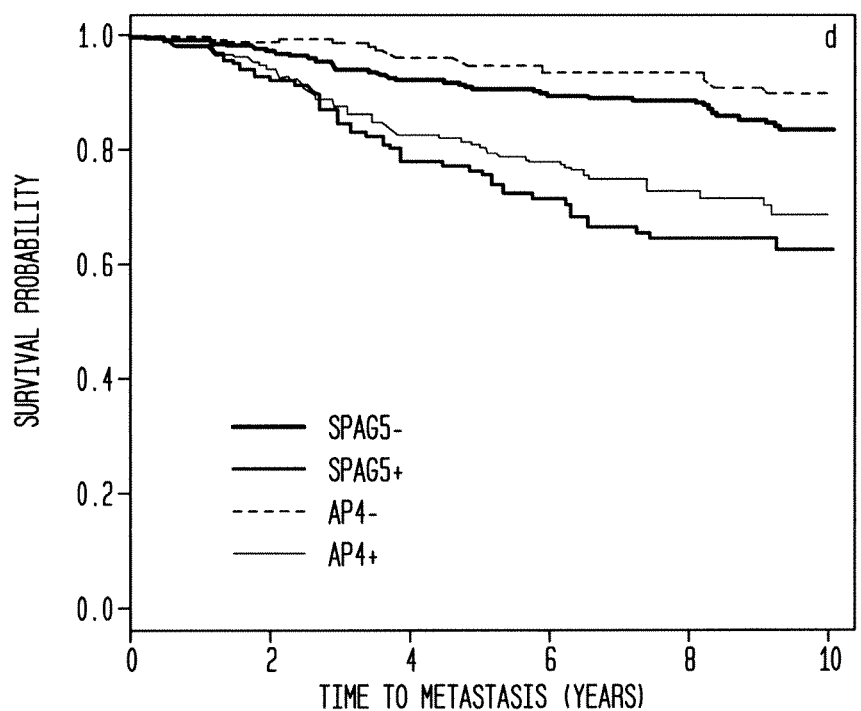

As reported in FIG. 2, the AP4− group has a 10 year metastasis-free survival probability of 0.90. This is comparable to that obtained with Mammaprint.

EXAMPLE 5

Use of AP4 Accelerated Progression Relapse Test to Determine Breast Cancer Prognosis in a Patient This example provides a method for using the AP4 test to provide a prognosis to an individual patient suffering from ER+ breast cancer.

A physician is desirous to provide an ER+ patient with a prognosis regarding the progression of her cancer and treatment options. Accordingly, a sample of the patient's breast tumor is taken and mRNA is extracted and subject to analysis via an Affymetrix® GeneChip® having multi-state probes for the genes MKI67, CDC6, and SPAG5 (212020_s_at, 212022_s_at, 203967_at, and 203145_at respectively).

The expression data obtained from the Affymetrix® GeneChip® is then compared to density distributions based on, for example, a mixture model fit for expression levels for an ER+ patient population. This comparison may be done manually or by a computer. The AP status for each of the four genes is determined. If the patient has a relatively high expression level as measured by at least one multi-state probe, the patient's AP status is AP4+ and the prognosis is deemed not good and chemotherapy is recommended. If the patient has a relatively low expression level as measured by all four of the multi-state probes, the patient's AP status is AP4− and the patient is deemed to have a good prognosis and no chemotherapy is recommended.

The AP4 test improves on the prognostic power of each of the individual probes in the test. A preliminary step in calculating AP4 is a partition of the samples in a cohort into CDC6+/−, MKI67+/−, etc. The binary variables representing these partitions can be merged to represent partitions for each probe ranging over the full validation set. The Kaplan-Meier plots for each probe, juxtaposed with the AP4+/− plot, are found in FIG. 6. While each probe yields a significant partition, none of the probes is as significant as AP4, as measured by the hazard ratio.

EXAMPLE 6

AP4 Improves on the Prognostic Power of Clinical Variables

A biomarker for relapse is only useful if it improves on the prognostic power of the standard clinical variables, such as tumor grade, size and lymph node status. AP4 is significant in multivariate analysis and in stratified analysis on clinically defined subtypes. This study is performed on the 738 samples in the study for which data is available on distant metastasis, tumor grade, size and lymph node status. Tumor size is represented here by a binary variable that is 0 for tumors <2 cm in diameter and 1 for tumors ≥2 cm.

The AP4 test improves on the clinical variables in a multivariate Cox proportional hazard model. The p-values for the clinical variables in univariate models are: grade, p=5.6×10$^{-5}$; node status, p=0.02; size, p=4.6×10$^{-7}$. The p-value for grade, node status and size together is 9.0×10$^{-8}$, while adding AP4 to these 3 gives p=2.4×10$^{-15}$. Comparing log-likelihoods, the level of significance of AP4 over grade+node status+size is 5.8×10$^{-11}$. Note that the distribution of lymph node status in the full dataset is distorted by the fact that some cohorts contain only node negative samples (see Table 2).

AP4 is found to be statistically significant on each of the subtypes defined individually by grade, size and lymph node status. The Kaplan-Meier plots are found in FIGS. 7 (a)-(g). Good prognosis groups are formed by combining clinical subtypes. AP4 is statistically significant on the set of lymph node negative tumors that are <2 cm in diameter (FIG. 7h). On the grade 2 tumors in this latter subgroup the p-value for AP4 is not below the significance threshold, however the Kaplan-Meier plot (FIG. 5i) does show a pronounced divergence in expected survival for AP4− and AP4+. Most of the sets formed by intersecting three clinical subgroups are too small for meaningful analysis. The 10-year expected survival probability in AP4− is nearly constant across all of these clinical subgroups, even poor prognosis groups such as grade 3 or LN+.

EXAMPLE 7

Use of the Accelerated Progression Relapse Test to Determine Prognosis of Patients Suffering from a Pathology Suitable for Analysis with the Accelerated Progression Relapse Test The accelerated progression (AP) relapse test for identifying multi-state genes that are correlated with disease progression can be applied to any disease state that is biologically homogeneous. For example, the AP relapse test can be applied to an cancer subtype that is biologically homogenous. In a homogeneous class of adenocarcinomas, in which mitotic factors are a key feature of disease progression, an effective panel similar to the panel of genes tested for breast cancer as described herein can be developed.

(a) Lung Cancer

Two multi-state genes were identified as generating a clinical useful test for stage I lung cancer. The dataset used was found in the National Cancer Institute caARRAY database, and is identified by experiment identifier jacob-00182. In this case, the test identifies an especially poor prognosis group of patients who should received chemotherapy. The probes are p=Affymetrix® Probe No. 218057_x_at (GenBank Accession No. NM_006067) and q=Affymetrix® Probe No. 04753_s_at (GenBank Accession No. AI810712). In contrast to the breast cancer and colon cancer studies described herein, poor prognosis is associated with low expression of p or q. That is, the good prognosis patients (LC (lung cancer)+) are those having both p+ and q+, while the poor prognosis patients (LC−) are those having either p− or q−. In a validation of 119 samples, 27% of the LC− patient die within 5 years, while only 12.5% of the LC+ patients die in 5 years. This degree of poor prognosis in LC− calls for aggressive treatment including chemotherapy.

The distribution of each gene's expression based on multi-state probe data provides a mixture model fit of the data show a bimodal distribution characteristic of multi-state genes necessary for determining the AP status of the patient according to the method of the invention. The data is pooled from 276 patient samples of stage I lung cancer patients and based on the pooled data, an individual patient's expression levels of each gene of interest are compared to the expression levels of the pooled data. If the patient has a relatively high expression of both genes associated with the multi-state probes, the patient is not recommended for treatment of lung cancer, such as chemotherapy. If the patient has a relatively low expression of at least one of the two genes of interest, the patient's prognosis is poor and the patient is recommended for treatment for lung cancer, such as chemotherapy.

(b) Colon Cancer

NOX4, a gene encoding a protein that generates reactive oxidative species which lead to blood vessel growth and invasion of tumors into surrounding tissue has been identified as a multi-state gene with relevance to determining the prognosis of patients suffering from colon cancer. The algorithm used to generate the AP status for ER+ breast cancer patients as described herein was applied to microarray data from three cohorts of colon cancer patients with disease stage I, II, and III, i.e., colon cancer patients whose cancer has not yet metastasized. Based on datasets GSE12945, GSE17536, GSE17537, the method identified a single probe (Affymetrix Probe No. 219773_at; GenBank Accession No. NM_016931) which is multi-state in all databases so that the p− patients have sufficiently good prognosis to excuse them from chemotherapy. This test was validated on 135 patients. The probe associated with the NOX4 gene, UNIGENE ID Hs.50507.

The distribution of NOX4 gene expression based on a mixture model fit of the data demonstrates a bimodal distribution characteristic of multi-state genes necessary for determining the AP status of the patient according to the method of the invention. Expression data was pooled from 228 patient samples from colon cancer patients with disease stage I, II, or III and based on the pooled data, an individual patient's expression levels of each gene of interest are compared to the expression levels of the pooled data. If the patient has a relatively high expression of NOX4, the patient is recommended for treatment of colon cancer, such as chemotherapy. If the patient has a relatively low expression of NOX4, the patient's prognosis is good and the patient is deemed not to benefit from further treatment of colon cancer, such as chemotherapy.

EXAMPLE 8

Comparison Between MapQuantDX™ and AP Relapse Test

The purpose of this example is to show that the AP relapse test of the present invention is a more accurate test when compared to other commercially available methods of grading breast cancer tumors and the prognosis for relapse. For example, the MapQuantDX™ (IPSOGEN, Marseille, France) is a molecular diagnostic test that measures tumor grade, a consensus indicator of tumor proliferation, risk of metastasis, and response to chemotherapy. MapQuantDX™ uses the genomic grade index (GGI). The GGI was developed using the same Affymetrix® array platform as used in the AP4 test according to one embodiment of the invention. The formula defining the GGI risk predictor, published in Sotiriou et al., Natl. Cancer Inst. 98(4):262-71, 2006, is used to compare accuracy between prognostic outcomes of the MapQuant DX™ and the AP Relapse Test of the present invention. In comparing accuracy of prognostic outcomes of the MapQuant DX™ and the AP Relapse Test of the present invention, the probability that MapQuant DX™ is as accurate as the AP Relapse Test is 0.002. In other words, in technical terms, the probability that the MapQuant DX™ outcome is not improved by performing the AP Relapse Test of the invention is p<0.002 or the probability that the MapQuant DX™ is as accurate as the AP Relapse Test is p<0.002.

Because of its heightened accuracy, the AP Relapse test has fewer false negatives and a stronger ability to identify patients who will and will not respond to further chemotherapy or other cancer treatment. In contrast, MapQuant DX™ has a higher incidence of identify patients as having a good prognosis when in fact, their prognosis is not good and chemotherapy should be administered. Accordingly, the AP Relapse test of the present invention provides a more accurate prognostic tool for determining a patient's need for further therapeutic intervention in treating breast cancer. See, for example, FIGS. 6A and 6B which show that the AP4 status has more accuracy than merely relying the individual genes alone.

EXAMPLE 9

Comparison of the OncoTypeDX® and the AP Relapse Test

The Oncotype DX® assay is a 21-gene assay that provides an individualized prediction of chemotherapy benefit and 10-year distant recurrence to inform adjuvant treatment decisions in certain women with early-stage breast cancer. The Oncotype DX® assay uses the MKI67 gene to determine the prognostic outcome for a patient. In comparing the prognostic ability of the Oncotype DX® assay to the prognostic ability of the AP relapse test of the present invention, the prognostic ability of the AP relapse test is more accurate and adds more prognostic power over MKI67 alone.

The Oncotype DX® assay was developed for use on ER+, lymph node− (LN−) patients. Accordingly, when lymph node positive (LN+) patients are included in the population of patients being tested, the prognostic accuracy of the Oncotype DX® assay decreases. As a result, applying the Oncotype DX® assay to LN+ patients excuses from chemotherapy a large number of patients who will metastasize. In contrast, the prognostic power of the AP relapse test of the present invention are equally applicable and accurate with respect to lymph node positive (LN+) and lymph node negative (LN−) breast cancers, whereas the Oncotype DX® assay is not as accurate its prognostic abilities with respect to LN+ breast cancers. In Accordingly, the Oncotype DX® assay is not as powerful a prognostic tool as the AP relapse test of the present invention.

EXAMPLE 10

Protein Staining Accelerated Progression Relapse Test

There is a strong indication that AP+/− status of genes of interest can be determined by immunohistochemistry (IHC). As explained herein, expression levels of multi-state genes determined by staining, for example, staining a patient tumor sample with the MIB-1 antibody for MKI67, appears to correspond well to the expression levels alternatively detected by microarray methods, with a threshold determined by the same mixture model fit methods as applied to the microarray data.

Staining for CDC6 and partitions lung cancer tissues into those that positively express the gene and those with negative expression. Staining for CDC45L partitions tissues into those that are growing rapidly and those that are more benign. In all of these cases, the monoclonal antibody effectively stains in formalin-fixed paraffin-embedded tissue.

It is anticipated that the present protocol maybe developed for an IHC-based test. Alternatives also exist for the test that can measure mRNA concentrations from paraffin-embedded tissue. Further, reverse transcriptase PCR is another method by which expression levels of genes can be ascertained according to the invention.

Immunohistochemistry methods are also suitable for detecting the expression levels of the genes of interest of the present invention. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, florescent labels, hapten labels such as biotin or an enzyme such as horseradish peroxidase or alkaline phosphatase. Alternatively, unlabeled primary antibody is used in conjunction with a labeled secondary antibody comprising antisera, polyclonal antisera or a monoclonal antibody specific for the primary antibody. Immunohistochemistry protocols and kits are well known in the art and are commercially available.

The present example is presented to demonstrate the utility of the present diagnostic predictive tests for ER+ breast cancer by using a method that includes a protein staining technique. For example, the +/− status of the genes used in order to determine a patient's prognosis based on the accelerated progression relapse test of the invention can be determined by staining breast cancer tumor tissue to determine the presence of proteins resulting from multi-state gene expression, as an alternative to using microarray detection with tumor mRNA.

For example, antibodies to each of MK167, CDC6 and SPAG5 genes' expressed proteins are obtained and linked to a reporter enzyme or fluorophore according to standard techniques. Preferably, the antibodies are monoclonal antibodies. Thin tissue slices of each patient tumor is subject to staining with antibody-reporter complex and visualized to ascertain the concentration of the expressed proteins from the MK167, CDC6, and SPAG5 genes according to standard protocols. Tissues from a variety of ER+ breast cancer patients are assayed according to this technique and analyzed for expression levels of the three proteins expressed from the MK167, CDC6, and SPAG5 genes. Based on the observed expression levels from the overall patient population, density distribution of the gene expression products is determined based on mixture model fit statistical analysis and the AP+/− status for each gene is determined for an individual patient and a prognosis is provided. AP4+ patients are given poor prognosis and recommended for chemotherapy while AP4− patients are given good prognosis and recommended to not have chemotherapy.

This has been verified for MK167 and CDC6 in studies by Viale et al. (Bibliography reference 22) and Karakaidos et al. (Bibliography reference 24).

EXAMPLE 11

Commercial Application of the Accelerated Progression Relapse Test

The purpose of this example is to illustrate how the AP relapse test of the invention may be utilized commercially for providing diagnosis and counseling to patients diagnosed with a disease state such as cancer.

In the first instance, a patient presenting with a cancer undergoes a tumor biopsy. A sample from the tumor is shipped to a certified pathology laboratory according to specifications designated by the test provider in order to preserve the sample. To ensure that the sample contains a sufficient percentage of cancerous cells to yield a reliable result, a pathologist will examine the tissue upon receipt of the sample at the laboratory. mRNA will be extracted from the tissue sample and analyzed according to designated protocols. Each analysis will be performed in triplicate and the results averaged for quality control. Analysis may be performed using a microarray or immunohistochemical staining or other technique know in the art for assessing the level of expression of a gene.

Following quantitative analysis of the extracted mRNA, a report will be prepared with details on the expression levels of each gene in the test, and the prognostic classification of the patient based on the AP status of the patient. The results of a large study of cancer patients will be included in the report, describing the probability of metastasis over 5 and ten years for a patient with the same test results. This report and all supporting materials on this patient will be reviewed and certified by a pathologist. The report will be transmitted to the physician requesting the test. The physician will then provide a prognosis to the patient based on the information in the report.

BIBLIOGRAPHY

The following references hereby specifically incorporated herein by reference in their entirety.
1. Fisher et al. (2004), *Lancet* 364, 858-68.
2. Paik et al. (2004), *N. Engl. J. Med.* 351, 2817-26.
3. de Vijver et al. (2002), *N. Engl. J. Med.* 347, 1999-2009.
4. Goldhirsch et al. (2005), *Ann. Oncol.* 16, 1569-83.
5. Eifel et al. (2001), *J. Natl. Cancer Inst.* 93, 979-89.
6. Paik et al. (2006), *J. Clin. Oncol.* 24, 3726-34.
7. Buyse et al. (2006), *J. Natl. Cancer Inst.* 98, 1183-92.
8. Zujewski et al. (2008), *Future Oncology (London, England)* 4, 603-10.
9. Piccart-Gebhart et al. (2007), *Ann. Oncol.* 18 Suppl 12, xii2-7.
10. Cardoso et al. (2008), *J. Clin. Oncol.* 26, 729-35.
11. Hanahan et al. (2000), *Cell* 100, 57-70.
12. Simpson et al. (2005), *J. Pathol.* 205, 248-54.
13. Sotiriou et al. (2006), *J. Natl. Cancer Inst.* 98, 262-72.
14. Fan et al. (2006), *N. Engl. J. Med.* 355, 560-9.
15. Colozza et al. (2005), *Ann. Oncol.* 16, 1723-39.
16. Liontos et al. (2007), *Cancer Res.* 67, 10899-909.
17. Yang et al. (2006), *Biochem. Biophys. Res. Commun.* 343, 428-34.
18. Pollok et al. (2007), *FEBS J* 274, 3669-84.
19. Rizki et al. (2007), *Cancer Res.* 67, 11106-10.
20. Tordai et al. (2008), *Breast Cancer Res.* 10, R37.
21. Scholzen et al. (2000), *J. Cell. Physiol.* 182, 311-22.
22. Viale et al. (2008), *J. Natl. Cancer Inst.* 100, 207-12.
23. Ahlin et al. (2007), *Histopathology* 51, 491-8.
24. Karakaidos et al. (2004), *Am. J. Pathol.* 165, 1351-65.
25. Aubele et al. (2000), *Diagn. Mol. Pathol.* 9, 14-9.
26. Wu et al. (2004), *Journal of the American Statistical Association* 99, 909-917.
27. Leisch (2004), *Journal of Statistical Software* 11:8.
28. U.S. Pat. No. 7,171,311—Hongyue et al.
29. U.S. Patent Publication 2010/0009861 Wang et al.
30. Jorgensen, et al. (2007), *The Oncologist*, 12(4): 397-405.
31. Ivshina et al. (2006), *Cancer Res.* 66(21):10292-301.
32. NCBI, Gene Expression Omnibus, Microarray datasets GSE4922; dataset GSE6532; dataset GSE7390; dataset 9195; dataset 11121, dataset GSE12945, dataset GSE17536, and dataset GSE17537.
33. Loi et al. (2007), *J. Clin. Oncol.* 25(10): 1239-46.
34. Loi et al. (2008), *BMC Genomics,* 9:239.
35. Desmedt et al. (2007), *Clin. Can. Res.,* 13(11): 3207-14.
36. Schmidt et al. (2008), *Cancer Res.,* 68(13): 5405-13.
37. Ross et al. (1994), *J. Clin. Pathol.,* 48:M113-M117.
38. U.S. Pat. No. 7,056,674, Baker et al.
39. Taylor et al. (2009), *Nature Biotechnology,* 27(2):199-204.
40. Fan et al. (2006), *N Engl J Med,* 355(6):560-9.
41. Gentleman et al. (2005), Bioinformatics and Computational Biology Solutions Using R and Biconductor, Springer-Verlag, Berlin/Heidelberg/New York.
42. Sotiriou et al. (2006), *J Natl Cancer Inst,* 98(4):262-72.
43. Sorlie et al. (2001), *Proc. Natl. Acad. Sci. USA* 98:10869-10874.
44. Kapp et al., (2006), *BMC Genomics* 7:231.
45. Tibshirani et al. (2002), *Proc Natl Acad Sci USA* 99(10): 6567-72.
46. Irizarry et al. (2006), *Bioinformatics* 22(7):789-794.
47. Gong et al. (2007), *Lancet Oncol.* 8:203-11.
48. Du et al. (2008), *Biochem Biophys Res Commun* 370(2): 213-9.
49. Habel et al. (2006), *Breast Cancer Res.* 8:R25.
50. Schmidt et al. (2004), *J Cell Biochem* 91:1280-92.
51. Buechler (2009), *BMC Cancer* 9:243.
52. Golub et al. (1999), *Science* 286:531 537.
53. Bhattacharjae et al. (2001), *Proc. Natl. Acad. Sci. USA* 98:13790 13795.
54. Chen-Hsiang et al., (2001), *Bioinformatics* 17 (Suppl. 1): 5316 5322.
55. Ramaswamy et al., (2001), *Proc. Natl. Acad. Sci. USA* 98:15149 15154.
56. Martin et al. (2000), *Cancer Res.* 60:2232 2238.
57. West et al., (2001), *Proc. Natl. Acad. Sci. USA* 98:11462 11467
58. Yan et al., (2001), *Cancer Res.* 61:8375 8380.
59. Perou et al. (2000), *Nature* 406:747 752.
60. National Cancer Institute caARRAY database, dataset identified by experiment identifier jacob-00182.

What is claimed:

1. A method of administering an aggressive breast cancer treatment comprising chemotherapy and/or radiation to an ER+ human breast cancer patient, said method comprising:
   providing a primary ER+ breast tumor tissue that has been surgically removed from a breast cancer patient;
   assaying mRNA expression levels of a gene panel consisting of a CDC6, MKI67, and SPAG5 gene in the primary ER+ breast tumor tissue;
   comparing said mRNA expression levels to the mRNA expression levels of the gene panel in a reference population of ER+ breast tumor tissues; and
   administering an aggressive breast cancer treatment comprising chemotherapy and/or radiation to the ER+ human breast cancer patient when the primary ER+ breast tumor tissue has a higher mRNA expression level than the level in the reference population for at least one gene in the gene panel, or not administering an aggressive breast cancer treatment comprising chemotherapy and/or radiation to the ER+ human breast cancer patient when the patient primary ER+ breast tumor tissue has a lower mRNA expression level of each gene of the gene panel consisting of a CDC6, MKI67, and SPAG5 gene than the mRNA expression level of each gene of the gene panel in the reference population.

2. The method of claim 1, wherein the mRNA expression level from the reference population demonstrates a bimodal density distribution having a defined threshold, whereby expression levels below the threshold are deemed low and expression levels above the threshold are deemed high.

3. The method of claim 1, further comprising a step of creating an electronic report of the results of the comparison between the mRNA expression levels in the primary ER+ breast and the reference population.

4. The method of claim 1, wherein one or more of the steps is performed by an appropriate computer software program on a computer.

5. The method of claim 1, wherein assaying the expression level is performed by microarray analysis with probes specific to the genes of the gene panel.

\* \* \* \* \*